United States Patent
Nicolson et al.

(10) Patent No.: US 11,968,299 B2
(45) Date of Patent: Apr. 23, 2024

(54) ENCRYPTION SYSTEM FOR MEDICAL DEVICES

(71) Applicant: Becton, Dickinson and Company, Franklin Lakes, NJ (US)

(72) Inventors: Strett Roger Nicolson, Owings Mills, MD (US); Larry Greenspan, Sparks, MD (US); Michael Fenske, Stewartstown, PA (US); Paul Fieni, Sparks, MD (US); Mark Larsen, Sparks, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 18/059,219

(22) Filed: Nov. 28, 2022

(65) Prior Publication Data
US 2023/0086295 A1    Mar. 23, 2023

Related U.S. Application Data

(62) Division of application No. 16/335,130, filed as application No. PCT/US2017/052807 on Sep. 21, 2017, now Pat. No. 11,522,692.

(Continued)

(51) Int. Cl.
*H04L 9/08* (2006.01)
*H04L 9/40* (2022.01)

(52) U.S. Cl.
CPC ........ *H04L 9/0866* (2013.01); *H04L 63/0428* (2013.01); *H04L 63/06* (2013.01);
(Continued)

(58) Field of Classification Search
CPC .... G16H 10/40; G16H 10/60; H04L 2209/88; H04L 63/0428; H04L 63/06; H04L 63/166; H04L 63/168; H04L 9/0866
See application file for complete search history.

(56) References Cited

U.S. PATENT DOCUMENTS

| | | | | |
|---|---|---|---|---|
| 6,577,734 B1 * | 6/2003 | Etzel | ..................... | H04L 9/0822 380/273 |
| 7,048,687 B1 * | 5/2006 | Reuss | ................ | A61B 5/14542 600/338 |

(Continued)

FOREIGN PATENT DOCUMENTS

| | | |
|---|---|---|
| CN | 101087350 | 12/2007 |
| CN | 102882847 | 1/2013 |

(Continued)

OTHER PUBLICATIONS

Supplementary European Search Report in European Application No. EP 17853935, dated Mar. 18, 2020, in 9 pages.

(Continued)

*Primary Examiner* — Sharon S Lynch
(74) *Attorney, Agent, or Firm* — Knobbe, Martens, Olson & Bear LLP

(57) ABSTRACT

Certain aspects relate to encryption systems and methods for medical devices. A medical device can include a connectivity module for establishing a communication channel with a cloud system. After obtaining a test result, the device can generate an unencrypted data block comprising a device identifier and an encrypted data block comprising a serial number of the device and the test result using an encryption key associated with the device identifier. The device can securely send the test result to the cloud system by transmitting the unencrypted data block and the encrypted data block to the cloud system via the communication channel.

20 Claims, 11 Drawing Sheets

Related U.S. Application Data

(60) Provisional application No. 62/399,197, filed on Sep. 23, 2016.

(52) U.S. Cl.
CPC .......... *H04L 63/166* (2013.01); *H04L 63/168* (2013.01); *H04L 2209/88* (2013.01)

(56) References Cited

U.S. PATENT DOCUMENTS

| | | | | |
|---|---|---|---|---|
| 7,587,368 B2 * | 9/2009 | Felsher | ............... | G06F 21/6245 705/52 |
| 7,712,131 B1 * | 5/2010 | Lethe | ....................... | G06F 21/57 726/20 |
| 7,974,924 B2 * | 7/2011 | Holla | ........................ | H04L 9/14 705/51 |
| 8,260,709 B2 * | 9/2012 | Holla | .................... | G06F 21/602 380/231 |
| 8,806,209 B2 * | 8/2014 | Hemphill | .............. | H04L 9/0819 713/171 |
| 9,312,926 B2 * | 4/2016 | Neafsey | ............... | G06F 21/6236 |
| 9,674,879 B2 * | 6/2017 | Hemphill | ................ | H04W 8/26 |
| 9,774,451 B2 * | 9/2017 | Motika | ................ | H04W 12/06 |
| 9,980,140 B1 * | 5/2018 | Spencer | ................ | H04W 12/02 |
| 10,111,268 B2 * | 10/2018 | Neafsey | ............... | H04B 5/0031 |
| 10,380,376 B2 * | 8/2019 | Gervais | ............... | G06F 21/6245 |
| 10,541,056 B2 * | 1/2020 | Booker | ................ | G06F 16/951 |
| 10,576,290 B2 * | 3/2020 | Schilling | ............ | A61N 1/37252 |
| 10,925,102 B2 * | 2/2021 | Neafsey | ............ | H04W 12/0431 |
| 2002/0010679 A1 * | 1/2002 | Felsher | ............... | G06F 21/6245 705/51 |
| 2002/0077985 A1 * | 6/2002 | Kobata | ................... | G06F 21/10 713/189 |
| 2004/0140898 A1 * | 7/2004 | Reeves | .................... | G06F 1/163 340/573.1 |
| 2004/0255023 A1 * | 12/2004 | Motoyama | .......... | H04L 41/0856 709/224 |
| 2006/0155584 A1 * | 7/2006 | Aggarwal | .............. | G16H 40/67 705/3 |
| 2006/0161054 A1 * | 7/2006 | Reuss | ........................ | A61B 5/00 600/338 |
| 2007/0061571 A1 * | 3/2007 | Hammes | ................. | G06F 21/31 713/168 |
| 2007/0138253 A1 * | 6/2007 | Libin | ...................... | G16H 10/60 235/375 |
| 2007/0232885 A1 * | 10/2007 | Cook | ....................... | G16H 30/40 600/407 |
| 2008/0103370 A1 * | 5/2008 | Dicks | .................... | G16H 15/00 600/300 |
| 2008/0235055 A1 * | 9/2008 | Mattingly | .............. | G16H 10/40 705/2 |
| 2011/0251960 A1 * | 10/2011 | Holla | .................... | G16H 30/20 705/51 |
| 2013/0024382 A1 * | 1/2013 | Dala | .................. | H04L 63/0464 705/51 |
| 2013/0059541 A1 * | 3/2013 | Sloan | .................... | H04W 12/50 455/41.2 |
| 2013/0066562 A1 * | 3/2013 | Hengstler | .............. | G16H 40/40 702/19 |
| 2014/0012843 A1 * | 1/2014 | Soon-Shiong | .......... | H04L 67/12 707/736 |
| 2014/0181521 A1 * | 6/2014 | Hemphill | ................ | H04W 8/26 709/219 |
| 2014/0219453 A1 * | 8/2014 | Neafsey | ................ | H04W 12/50 455/41.1 |
| 2014/0258727 A1 * | 9/2014 | Schmit | .................. | G06F 21/445 713/182 |
| 2015/0063164 A1 * | 3/2015 | Hemphill | .............. | H04W 76/11 370/254 |
| 2015/0106619 A1 | 4/2015 | Spalka | | |
| 2015/0269331 A1 * | 9/2015 | Bolanos | .................. | G06F 21/34 705/51 |
| 2015/0297306 A1 * | 10/2015 | Lazar | ...................... | A61B 5/091 600/543 |
| 2015/0350008 A1 * | 12/2015 | Kim | .................... | H04L 12/2816 709/221 |
| 2016/0227593 A1 * | 8/2016 | Neafsey | ............... | H04B 5/0031 |
| 2016/0232010 A1 * | 8/2016 | Dicks | .................... | G16H 40/67 |
| 2016/0234022 A1 * | 8/2016 | Motika | ................ | H04W 12/06 |
| 2016/0253367 A1 * | 9/2016 | Spalka | ................ | G06F 21/6227 713/167 |
| 2016/0267295 A1 * | 9/2016 | Gervais | .................. | G16H 10/40 |
| 2016/0306920 A1 * | 10/2016 | Soon-Shiong | ......... | G16B 30/10 |
| 2017/0076050 A1 * | 3/2017 | Soon-Shiong | ......... | G16H 30/40 |
| 2017/0177724 A1 * | 6/2017 | Booker | .................. | G16H 50/80 |
| 2018/0028827 A1 * | 2/2018 | Schilling | ................ | A61N 1/00 |
| 2018/0263495 A1 * | 9/2018 | Cronin | .............. | A61B 5/14551 |
| 2019/0006028 A1 * | 1/2019 | Soon-Shiong | ......... | G16H 30/20 |
| 2019/0059122 A1 * | 2/2019 | Neafsey | ................ | H04W 12/04 |
| 2019/0364389 A1 * | 11/2019 | Hernoud | ................ | G01C 21/20 |
| 2019/0379644 A1 * | 12/2019 | Schneider | ............ | H04L 9/0894 |
| 2020/0196108 A1 * | 6/2020 | Hernoud | ................ | H04L 41/06 |
| 2020/0197711 A1 * | 6/2020 | Schilling | ............ | A61N 1/37254 |
| 2020/0273549 A1 * | 8/2020 | Soon-Shiong | ......... | G16B 20/40 |
| 2021/0256336 A1 * | 8/2021 | Hill | .................. | G06K 19/06037 |

FOREIGN PATENT DOCUMENTS

| | | |
|---|---|---|
| CN | 104137467 | 11/2014 |
| CN | 105849744 | 8/2016 |
| CN | 105871857 | 8/2016 |
| DE | 10-2012-021719 | 5/2014 |
| EP | 2731040 | 5/2014 |
| EP | 2822214 | 1/2015 |
| JP | 2014-089631 | 5/2014 |
| WO | WO 2013/129056 | 7/2015 |
| WO | WO 2015/143309 | 9/2015 |
| WO | WO 2016/067862 | 5/2016 |
| WO | WO 2018/057801 | 3/2018 |

OTHER PUBLICATIONS

International Search Report and Written Opinion dated Sep. 21, 2017 for PCT patent application No. PCT/US17/52807.
Search Report from IP.com (dated Jun. 18, 2021) (Year: 2021).
Search Query Report from IP.com (dated Nov. 24, 2021) (Year: 2021).
Search Query Report from IP.com (dated Jun. 17, 2022). (Year: 2022).
Search Query Report from IP.com (dated Oct. 18, 2022) (Year: 2022).

* cited by examiner

| SCAN CONFIG BARCODE | S/N: XXXXXXXXXXXXX<br>Expiration: DD-MMM-YYYY<br>Tests Remain: xxxx<br>OID: Yes  SID: Yes  LOT: No<br>Language: English<br>FW Ver: X.XX | SCAN OPERATOR ID |
|---|---|---|
| SPECIMEN ID SCAN ENABLED | KIT LOT NUMBER SCAN ENABLED | OPERATOR ID:<br>XXXXXXXXXXXXXXXXXX<br><br>SCAN SPECIMEN ID |
| SPECIMEN ID SCAN DISABLED | KIT LOT NUMBER SCAN DISABLED | |
| OPERATOR ID SCAN ENABLED | | |
| OPERATOR ID SCAN DISABLED | | |

FIG. 9

ENCRYPTION SYSTEM FOR MEDICAL DEVICES

RELATED APPLICATIONS

The present application is a divisional of U.S. patent application Ser. No. 16/335,130, filed Mar. 20, 2019, which is a 371 National Stage Application of PCT Patent Application No. PCT/US2017/052807, filed Sep. 21, 2017, which claims priority to U.S. Provisional Application No. 62/399,197, filed Sep. 23, 2016, the contents of each of which are incorporated by reference in their entireties.

TECHNICAL FIELD

The systems and methods disclosed herein are directed to systems and methods for encrypting transmissions from medical testing, and, more particularly, to lateral flow assay devices.

BACKGROUND

In patient care, immunoassay technology provides simple and relatively quick means for determining the presence of analytes in a subject sample. Analytes are substances of interest or clinical significance that may be present in biological or non-biological fluids. The analytes can include antibodies, antigens, drugs, or hormones.

The analyte of interest is generally detected by reaction with a capture agent, which yields a device more easily detected and measured than the original analyte. Detection methods can include a change in absorbance, a change in color, change in fluorescence, change in luminescence, change in electrical potential at a surface, change in other optical properties, or any other easily measured physical property indicating the presence or absence of an analyte in a sample.

Some medical systems may be located remotely from a central server that stores and analyzes the measured analyte. For example, some systems may be located in a doctor's office, but transmit data to a central server across a wired or wireless connection.

SUMMARY

Immunoassay devices play an important role in areas such as clinical chemistry and have been made portable for use in the field. Assays are routinely performed to detect the presence of particular analytes that are present when a human or non-human subject has a particular disease or condition. For example, an assay as described herein can be used to detect whether a patient has flu A, flu B, RSV, group A strep, or another illness, is experiencing ovulation or pregnancy, or has a particular drug or chemical compound in their body, to name a few examples.

Such assays and assay reader devices are used by skilled clinicians and laypersons alike and may be located in a position remote to where a sample analysis is performed. Such assays and assay reader devices may be located in a location remote to the systems needed to maintain a complete patient history, and other record keeping systems that may be used in patient treatment activities, such as the pharmacy. Accordingly, an assay reader device according to the present disclosure is designed to be simple and reliable, for example by including a module for communicating directly to a central server system through a wired or wireless connection. The assay reader device may also have a simple barcode scan input of any needed additional information and by minimizing a number of steps required for the user to perform between sample application and result notification. The barcode scan input can provide for a high level of traceability and compliance by allowing clinics, laboratories, and the like to implement custom test result documentation standards. Some examples can enforce compliance with such standards at the reader level, for example by pre-configuring the readers to require input of designated types of information before transmitting results. As another example, communications between the reader and a centralized database can be used to ascertain whether transmitted test data complies with such standards and, if not, to send instructions back to the reader device to prompt a user for any missing information. These communications may be encrypted to ensure that any data or instructions transmitted between the assay device and centralized database are secure. Further, such assays and assay reader devices can be used in a variety of contexts, both inside and outside of the clinical setting. Accordingly, an assay reader device according to the present disclosure can include a module providing network connectivity capabilities for providing test results to one or more centralized databases.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 9 illustrates various examples of display text that can be presented to an operator on a display screen of an assay reader device as described herein.

DETAILED DESCRIPTION

Introduction

Figure 1A:
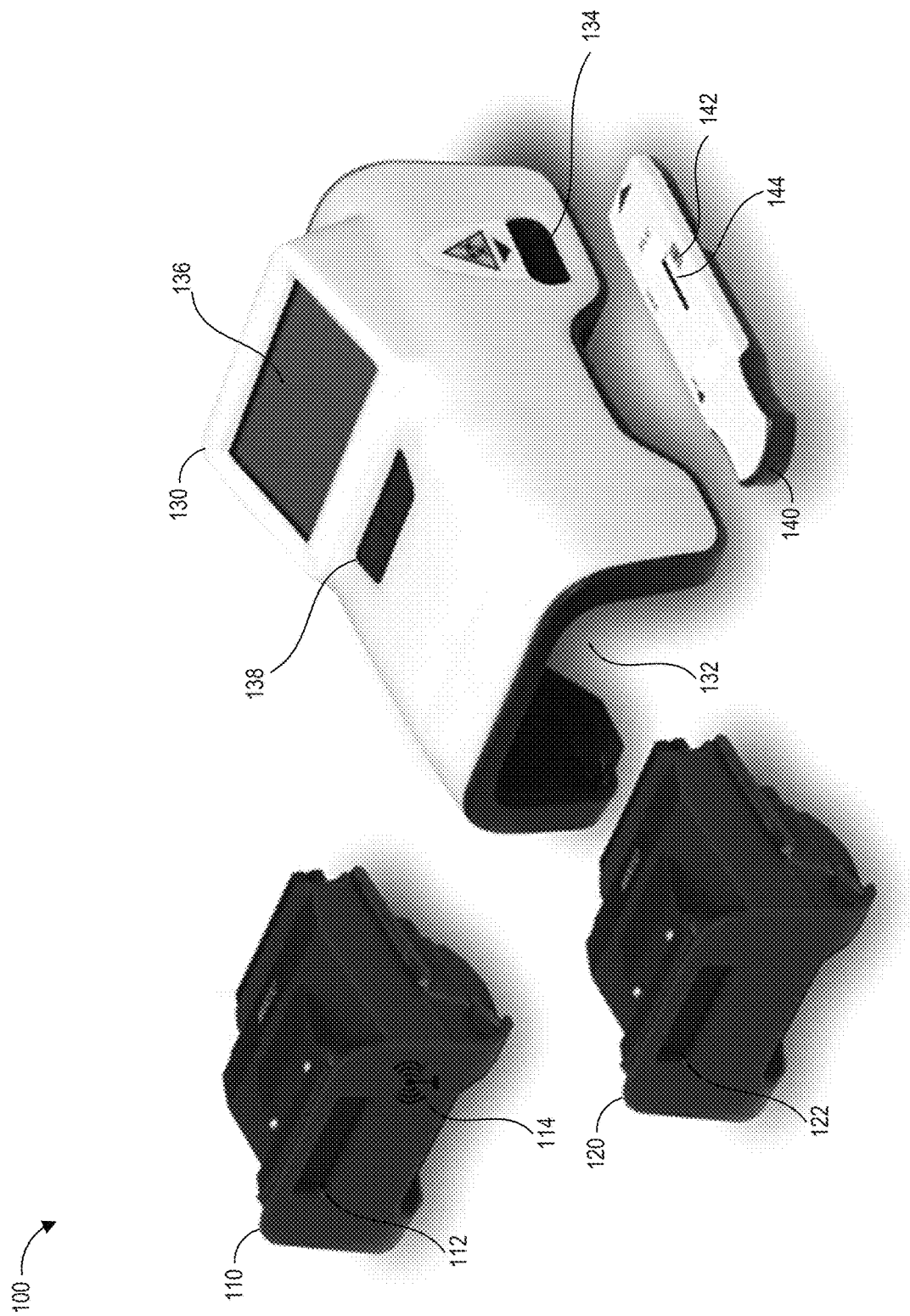
FIG. 1A illustrates an example set of components of an assay reader system.

Embodiments of the disclosure relate to systems and methods for modular assay reader devices. In one embodiment, the modular assay reader devices are configured to receive a number of different modules within their housing. In one example, the modules may include a barcode scanning input device and optional network connectivity capabilities. Embodiments of the reader devices can be portable, for example relatively small and light with an option to be powered by a battery or other local electrical storage. The disclosed reader devices can be used in hospitals, clinics, doctors' offices, and other patient care facilities to enable rapid detection and identification of numerous types of biological conditions, such as the presence of antibodies that indicate an infectious agent is present. A network connectivity module can enable standardizing, tracking and electronically connecting test results from reader devices located throughout a network for improved patient care.

One embodiment of the invention is a medical or assay device, such as described herein, that uses encrypted communications to ensure that any data or instructions transmitted between the assay device and centralized database are secure. In one embodiment, each assay device is assigned a globally unique identifier (GUID) that is permanently stored, or burned, into a special circuit within the assay device. During communications between the assay device and a central database system, the assay device can be authenticated by the database system by first confirming that the globally unique identifier is valid and matches a GUID stored in a database of authentic globally unique identifiers. To protect the globally unique identifier from being copied to an illegitimate device, the GUID may be transmitted in an encrypted channel to the central database. For example, during any authentication transmission of the globally unique identifier to a central database, it may be transmitted through an encrypted channel implementing transparent data encryption (TDE). The GUID may otherwise be unencrypted.

During manufacturing, the GUID of the assay device may be associated with a serial number of the device and an encryption key. When authenticating a transmission, the serial number encrypted with the associated encryption key may be transmitted with the GUID to the central database. If the GUID received by the central database is determined to be a valid GUID, the encryption key associated with the GUID can be used to decrypt the received encrypted serial number. If the decrypted serial number matches the serial number associated with the GUID, the device can be authenticated to the central database system.

One type of reader device is configured to read, or otherwise analyze, lateral flow assays, which can test for a wide variety of medical and environmental conditions or compounds. For example, lateral flow tests can rely on a form of immunoassay in which the test sample flows along a solid substrate via capillary action. Lateral flow assay reader devices can read lateral flow assay strips to detect the existence of a hormone, metabolite, toxin, or pathogen-derived antigen. This reading can be accomplished with the use of a detector containing one or more sensing elements, such as but not limited to a PIN detector, a linear array detector, a CMOS imager, and a CCD-based imaging device, which is configured to detect the presence or absence of a line on the lateral flow assay based on the presence or absence of a visual line on the assay. Some tests, implemented by assay reader devices, are designed to make a quantitative determination, but in many circumstances the tests are designed to return or indicate a positive/negative qualitative indication. Examples of assays that enable such qualitative analysis include blood typing, most types of urinalysis, pregnancy tests, and HIV/AIDS tests. The assay reader device can identify a result of such tests by autonomously following a pre-programmed decision-making process or rule. In addition to reader devices configured to analyze lateral flow assays, implementations of diagnostic reader devices described herein can analyze other types of assays, such as but not limited to molecular assays, and provide a diagnostic test result.

The assay reader device can be a single-step device wherein the user need only apply the sample prior to viewing the result and optionally having the result transmitted to appropriate hospital, laboratory, or medical record databases. Such a single-step device can obviate the necessity of performing complicated and time consuming processing steps that may introduce errors in the end result. For example, a user may press a single button on the assay reader device to power the device on. Thereafter, insertion of a sample cartridge into the device can automatically activate a reading process to determine and display a test result based on the sample cartridge without further user input. In some embodiments having network connectivity capabilities, the determined test result can additionally be automatically sent without requiring further user input to a remote storage device, for example to centralized database and then from the centralized database to a designated clinician or another database, for example a Hospital Information System (HIS), Laboratory Information System (LIS), or a database maintained by a public health agency like the CDC, FDA, and WHO. In some embodiments having network connectivity capabilities, the determined test result can be sent directly to the designated clinician or database. As used herein, a remote storage device can be the centralized database, HIS, LIS, public health agency database, device of a designated clinician, or any other data storage not physically coupled to the assay reader device.

The disclosed portable assay devices can include a base assay analyzer, such a base assay reader device, having a bay for receiving a number of different modules. One module can include a barcode scanner for use in user input of any needed additional information, for example patient identification information, test type, device operation mode, sample information, and any other additional test or patient information pertinent to the test performed by the IVD device. In some embodiments device operation mode can be set via a number or pattern of clicks of a single button of the base assay analyzer. Another module can include the barcode scanner and additionally a network connection element. Such a modular design approach allows the assay reader device to expand its functionalities, for example to provide barcode scanning and wireless connectivity, while maintain its portability and cost advantage. The selection of different modules provides the user with the flexibility to decide the best functional capabilities necessary for their own settings or applications. The module can be an optional accessory to the base assay analyzer, and the base assay analyzer can function without a module inserted to read inserted assays, for example lateral flow assay test strips. A module can be swapped among analyzers. Once inserted, the module can become an integral part of the analyzer.

As indicated above, one of the modules can include both a barcode reader and a communication component for network connectivity, for example via a wireless connection such as a cellular modem, satellite connection, or Wi-Fi, or via a wired connection. When such a module is inserted into a bay of the assay reader device and in electronic communication with a memory and/or processor of the device, the assay reader device becomes capable of sending or uploading data to a remote repository via a network. As such, the test data of such assay reader devices can be stored and analyzed, alone or in the aggregate, by remote devices or personnel. A module having a cellular or satellite modem provides a built-in mechanism for accessing publicly available networks, such as telephone or cellular networks, to enable direct communication by the assay reader device with network elements or other IVD devices to enable electronic test result transmission, storage, analysis and/or dissemination without requiring separate intervention or action by the user of the device. For example, in some cases, the electronic test result transmission, storage, analysis and/or dissemination occurs automatically upon a patient sample being analyzed by the assay reader device. In another example, the electronic test result transmission, storage, analysis and/or dissemination occurs immediately upon a patient sample being analyzed by the assay reader device. In some embodiments the module can provide connection to a cloud database, for example a server-based data store. The cloud based connectivity module can enable ubiquitous connectivity of assay reader devices without the need for a localized network infrastructure.

Using the barcode scanner, device users can customize an assay reader device to perform various workflows best fit to their environment and compliance requirements. This barcode scan approach offers a simple and error-free way for the end-user to customize a diagnostic device. For example, barcodes can be scanned to set a device operation mode or to specify required types of information to comply with requirements, such healthcare organization standards, compliance standards, documentation standards, reporting standards, or any other requirement applicable to the testing environment.

In some embodiments device operation mode can additionally or alternatively be set via a number or pattern of clicks of a single button of the base assay analyzer. For example, in some implementations a single press of the button can power on the base assay analyzer and set the analyzer to a default operation mode, and the device can implement the default operation mode upon insertion of a cartridge. A double click of the button can initiate an alternate operation mode that is different than the default operation mode. Other numbers or patterns of pressing the single button by a user can provide instructions to the processor of the device regarding a desired operation mode. Embodiments of a base assay analyzer are described herein with reference to a single button, but other features allowing a user to select and switch between device operation modes are possible (such as but not limited to a single switch, knob, lever, or handle).

One example of a device operation mode is end-point read mode. In the end-point read mode, the user prepares and incubates the assay outside of the base assay analyzer and tracks the development time of the assay. For example, a flu assay can have a development time of 10 minutes, so the user would apply the specimen to the assay and wait for 10 minutes. At the end of the 10 minutes the user would insert the assay into the base assay analyzer to obtain a test result. Accordingly, when operating in end-point read mode the base assay analyzer can provide instructions, for example audibly or on a visual display, that instruct a user to wait for a predetermined time after applying a sample to an assay before inserting the assay in the base assay analyzer. In other embodiments, when operating in end-point read mode the base assay analyzer may not display any instructions but may simply read an assay upon insertion into the base assay analyzer. Upon insertion of the assay into the base assay analyzer, an optical reader of the device can collect image data representing the assay for analysis in determining a result of the assay. In some embodiments end-point read mode can be the default operation mode of a base assay analyzer.

Another example of a device operation mode is walkaway mode. Accordingly, when operating in walkaway mode the base assay analyzer can provide instructions for the user to insert the assay immediately after or during application of the sample. In the walkaway mode according to one embodiment, the user can apply the specimen to the assay and immediately insert the assay into the base assay analyzer. The assay will develop inside the base assay analyzer and the base assay analyzer can keep track of the time elapsed since insertion of the assay. At the end of the predetermined development time, the base assay analyzer can collect image data representing the assay, analyze the image data to determine a test result, and report the test result to the user. The assay development time can be unique to each test, for example a flu assay development time can be 10 minutes and a strep assay development time can be 5 minutes. In some embodiments walkaway mode can be set by double-clicking the single button of the base assay analyzer. Further input can indicate the assay development time to the reader device. For example, a barcode scanned by the barcode reader of the inserted module, or a barcode provided on the assay or on a cartridge used to hold the assay, can indicate to the device a type of assay that is inserted and a development time for that assay. Based upon the type of assay, the base assay analyzer can wait for the predetermined amount of time after sample application and insertion before collecting image data representing the assay.

There are many advantages associated with the ability of a user to select and switch between device operation modes in implementations of base assay analyzers described herein. The endpoint read mode can be convenient in large laboratories or medical practice facilities where personnel typically batch process a number of tests. The walkaway mode can be useful when a single test is being performed, or when the end user does not want to have to track the assay development time (or is not knowledgeable or not trained on how to track the assay development time accurately). The walkaway mode can advantageously reduce or eliminate the occurrence of incorrect test results due to an assay being inserted and imaged too quickly (too soon before the development time of the assay has elapsed) or too slowly (too long after the development time of the assay has elapsed). Further, in walkaway mode the assay reader can operate to capture multiple images of the assay at predetermined time intervals, for example when a kinetic graph of the assay readings is desired.

One embodiment of the disclosed base assay analyzer, such as a base assay reader device described in detail below, includes only a single button on its exterior housing, such as a single power button that powers the base assay analyzer off and on. Embodiments of the disclosed base assay analyzer also implement two different device operation modes (although more than two device operation modes are possible). In order to enable the end user to select and switch between the two device operation modes, the base assay analyzer can include instructions to implement a double-click function on the power button. After receiving input of a single press of the button to power on the device, insertion of an assay cartridge can automatically trigger end-point read mode. When the processor of the device receives input from a user double clicking the power button, this can initiate the stored instructions to implement the walkaway mode. This double click functionality offers a simple and intuitive way for the end user to switch between different operational modes of the base assay analyzer. The double click functionality also enables the user to configure the device in real time to operate in the walkaway mode without requiring any additional configuration steps or additional programming of the base assay analyzer by the user. It will be appreciated that the base assay analyzer can be provided with instructions to recognize other click modes instead of or in addition to the double click to trigger secondary (non-default) device operation modes, for example to recognize a user pressing the button any predetermined number of times, pressing the button in a predetermined pattern, and/or pressing and holding the button for a predetermined length of time.

Other examples of barcode uses include, as described above, providing additional data for association with test result data, including patient identification information, test type, device operation mode, sample information, and any other additional test or patient information pertinent to the test performed by the IVD device. Some barcodes can unlock device functions. Some barcodes can provide or update various types of information the device uses to analyze an assay, determine a test result, or perform a function. For example, a scanned barcode can provide to the reader device assay or reader calibration information that is useful or necessary to perform the test. In embodiments in which the device does not have wireless network connectivity, test results can be stored in a memory of the device, and in order to access the stored test results a user can scan a password barcode using the barcode scanner.

Although the disclosed devices are typically described herein as assay reader devices, it will be appreciated that the modular system design and network connectivity aspects described herein can be implemented in any suitable in vitro diagnostic device. For example, features described herein can be implemented in reader devices that analyze other types of assays, such as but not limited to molecular assays, and provide a diagnostic test result.

Various embodiments will be described below in conjunction with the drawings for purposes of illustration. It should be appreciated that many other implementations of the disclosed concepts are possible, and various advantages can be achieved with the disclosed implementations.

Overview of Example Assay Reader Devices and Operations

Figure 1B:
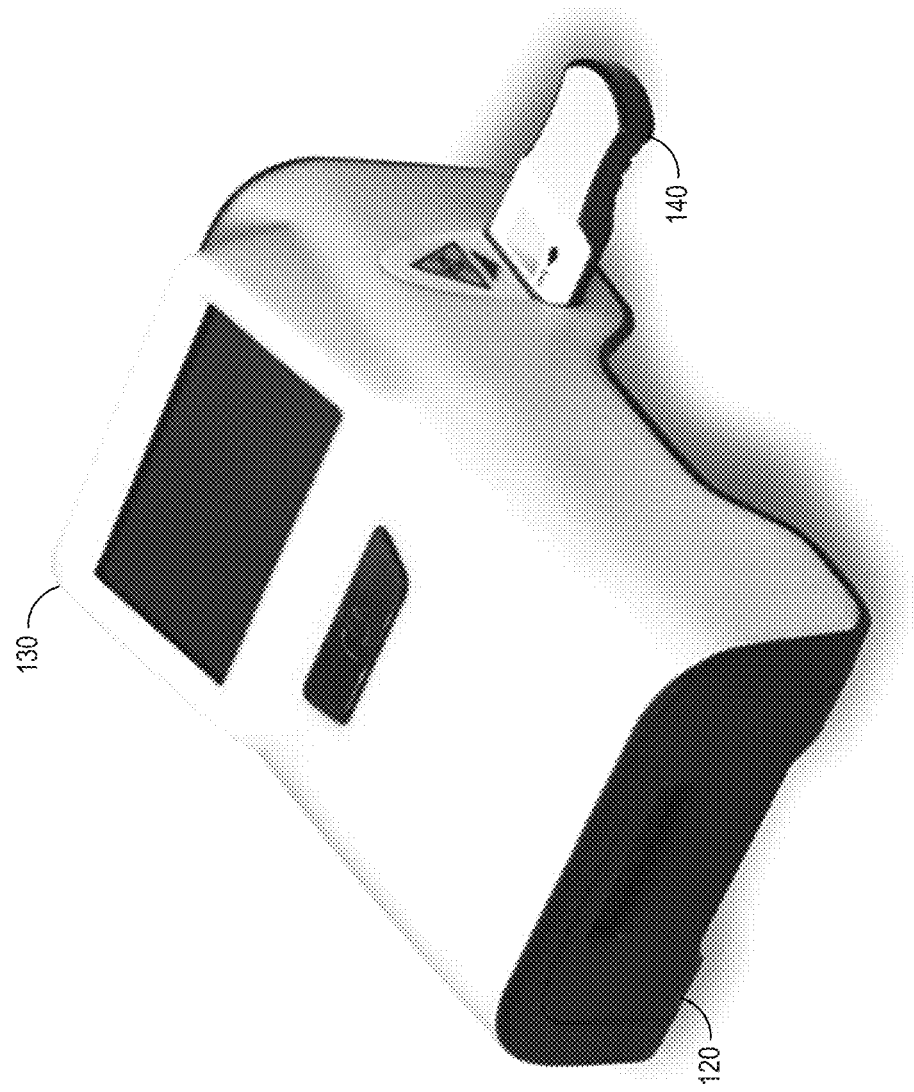
FIG. 1B illustrates an example assembled reader and module of the assay reader system of FIG. 1A.

FIG. 1A illustrates an example set of components of an assay reader system 100. The set of components includes a barcode module 120 and a barcode and connectivity module 110 that can be lockingly inserted into a bay 132 of a base assay reader device 130, and the set of components further includes a cartridge 140 for holding an assay 144 for insertion into the base assay reader device 130. FIG. 1B illustrates an example assembly of the base assay reader device 130 and barcode module 120 with the cartridge 140 inserted into a cartridge receiving aperture 134 of the reader 130. The components of FIGS. 1A and 1B will be discussed together in the discussion below.

Base assay reader device 130 includes a bay 132 for lockingly and optionally releasably receiving one of a number of different modules, a cartridge receiving aperture 134, a display 136, and a single button 138. The bay 132 can include both mechanical features for lockingly mating with corresponding mechanical features of an inserted module as well as electrical features for establishing electronic data communications with components of the inserted module. Base assay reader device 130 can be capable of providing basic assay analysis and data storage features without any inserted module, and an inserted module can be selected and inserted to expand upon the basic features. In embodiments in which no module is inserted, a cover can be provided over the opening of the bay 132. For example, the device 130 may be originally provided with the cover, and the cover can be removed to insert one of the interchangeable modules.

The cartridge receiving aperture 134 can be sized and shaped to align a test region of an assay with a detector or detector array provided within the device 130 when the assay is inserted through the cartridge receiving aperture 134. For example, if the assay is lateral flow assay test strip the test region can include one or more of a control zone and a test zone having immobilized compounds that are capable of specifically binding the target analyte. The detector can implement adaptive read technology to improve specificity of test results and to reduce false-positive results by compensating for background and non-specific binding. The base assay reader device 130 can be configured for fast and accurate assay performance, for example as a digital immunoassay configured for detecting Flu A+B, RSV and Group A Strep in 10 minutes or less. This can aid in rapid diagnosis and facilitate a test-and-act-approach while the patient is in the office.

Display 136 of base assay reader device 130 can be an LED, LCD, OLED, or other suitable digital display and can implement touch-sensitive technologies in some embodiments. Button 138 can be a mechanical button for powering on the base assay reader device 130. As described above, the device can include instructions to recognize a pattern of presses of the single button 138 in order to select a device operation mode. As discussed in more detail below, button 138 can provide users with secure, one-touch wireless electronic medical record synchronization when a connectivity module is inserted into the bay 132 of device. For example, a single press (or pattern of presses) of the simple one-touch button can ready the base assay reader device 130 for use, store test result data to the device memory, and transfer the test result to a patient electronic medical record through the connectivity module. Other embodiments of the device 130 may power on and be readied for use automatically when plugged in or otherwise powered and thus button 138 may be omitted. In other embodiments, multiple buttons can be provided on the device 130. The assay reader device can further include a processor and at least one memory, as discussed in more detail below. Base assay reader device 130 can be data storage and printing enabled.

Barcode module 120 includes a barcode scanner 122. Barcode scanner 122 can include one or more photodetectors and optionally light emitting devices for reading barcodes. For example, one implementation of barcode scanner 122 can include a light source, a lens for focusing the light source onto an object, and a light sensor for receiving light reflected off of the object and translating the received light into electrical signals. Some implementations of a sensor of barcode scanner 122 can include an array of many tiny light sensors such that a voltage pattern generated by the array is substantially identical to the pattern in a barcode. The barcode scanner 122 can also include decoder circuitry or software for analyzing the image data provided by the sensor, identifying a barcode pattern in the image data, determining content associated with the barcode pattern, and outputting the content, for example to a processor of the assay reader device. Barcode module 120 can further include mechanical features for lockingly engaging corresponding features within the bay 132 of the base assay reader device 130 and electronic features for establishing electronic data communications with components of the base assay reader device 130.

Though not illustrated, barcode module 120 can include an information element, for example a memory device or other active or passive electrical component. A passive information element can include transistor networks, PROMs, ROMs, EPROM or other programmable memory, EEPROM or other reprogrammable memory, gate arrays and PLAs to name a few examples. The information element can function to identify the capabilities of barcode module 120 to the assay reader and/or to authenticate the barcode scanning capabilities of barcode module 120 as a module from a specific source or manufacturer.

The barcode module 120 can ensure a high level of traceability and quality control via a customizable documentation functionality, data storage/download, and printing capability, while reducing manual transcription and risk of errors. As used herein, traceability can refer to the ability to verify the location, time, personnel, patient, or other information associated with a test performed using a reader device by means of documented information. The documented information can be advantageously accessed by numerous entities in a number of ways described herein. As described above, the barcode scanner can be used to enter test-related data, change device settings, unlock data access or other features, or to change the device mode. Test-related data can include user ID, clinician or test administrator ID, specimen ID, and test kit lot and/or expiration, among other test-related information described herein. Multiple operating modes for the assay reader device provide a flexible workflow implemented via barcode scanning.

With respect to traceability, a hospital, clinic, laboratory, or other healthcare organization can have internal standards specifying type(s) of information that are required to be recorded about each test performed in order for the test results to be compliant with applicable regulations. The barcode scanner can enable a clinician administering a test to input the required information by scanning a barcode. In some implementations, a barcode scanning module can be pre-programmed to output a listing of the required types of information associated with each test, or to output a prompt to a user to input any required information that has not been scanned before the test results are sent for storage. In some implementations, a barcode scanning module with connectivity functionality can communicate with a centralized database to provide a listing of the required types of information. The required types of information can be communicated wirelessly from the centralized database to the base assay reader device and displayed to the user. The user can input the required types of information by using the barcode scanning module to scan one of a plurality of available barcodes provided to the user. Once the barcodes associated with the required types of information have been scanned, the test result can be associated with the inputted information and sent securely, and in some cases automatically and/or wirelessly, to a laboratory information system and/or electronic medical record. The test result transmitted to the laboratory information system and/or electronic medical record is thus seamlessly and automatically associated with information (such as but not limited to user ID, clinician or test administrator ID, specimen ID, and test kit lot and/or expiration), significantly enhancing traceability of test results obtained using methods and systems described herein.

In some embodiments, a base assay reader device can allow the end-user to configure preset functions such as whether to require a patient ID barcode scan or Operator ID barcode scan at the start of each test. The configuration of these preset functions can be accomplished by scanning a configuration barcode that, once decoded by the device, includes instructions for the preset function scanning configuration. In one implementation, a healthcare facility administrator can initially select, from a set of printed barcodes, one or more barcodes corresponding to the types of information required by the administrator's desired configuration for a particular reader device; subsequent to this initial configuration selection, a user in the healthcare facility using the particular reader device can scan the appropriate barcodes to input information corresponding to the pre-selected functions of the reader device. The reader device can transmit all available information related to the test to a centralized server, for example via a connectivity module or a wired connection to another computing device. In one implementation, compliance may not be enforced at the reader level, and if the end user provided patient ID via barcode scan then this information will be transmitted with the test result, otherwise the patient ID fields will be left blank. Other implementations can prompt the end user for the missing information. Local data storage, download, and print options can help to ensure compliance and traceability if the readers do not have wireless or cellular connectivity capabilities.

To illustrate advantageous customization options with one non-limiting example, an administrator in a physician's office can select data categories A, B, and C and configure the reader devices within the office to transmit a report including data corresponding to categories A, B, and C, whereas an administrator in an acute care center can select data categories A, B, D, and E and configure the reader devices within the center to transmit a report including data corresponding to categories A, B, D, and E. The ability to customize reports can significantly reduce administrative and recordkeeping time. The obtained data can also comply with applicable compliance standards more often because opportunities to introduce human error in the reports are reduced.

FIG. 9 illustrates example display text that can be presented to an operator of an assay reader device. As described above, embodiments of the systems and methods described herein can allow the end-user to customize, on a particular assay reader device, the types of information that will be stored in association with test results, significantly increasing compliance and traceability of test results, and reducing transcription and documentation errors. In embodiments including wireless or cellular connectivity capabilities, customized reports including test results associated with selected information categories can be automatically transmitted to a remote server. The top display in the first column of the example displays in FIG. 9 illustrates a display of the assay reader device prompting the user to scan a configuration barcode in order to enable a particular type of information to be associated with test results, or to disable the particular type of information from being associated with the test results. In this non-limiting example, after reading the "SCAN CONFIG BARCODE" prompt, the user scans a barcode that instructs the assay reader device to enable an operator ID function (if the user wishes to associate and store operator ID information with test results), or the user scans a barcode that instructs the assay reader device to disable an operator ID function (if the user does not wish to associate and store operator ID information with test results). After the user scans the barcode indicating the user's selection, the assay reader device displays text confirming the user's selection. In this non-limiting example, the assay reader device displays "OPERATOR ID SCAN ENABLED" or "OPERATOR ID SCAN DISABLED" to the user. The assay reader device may then ask the user to enable or disable other types of information functions, such as but not limited to specimen ID and kit lot ID (see example display tests in FIG. 9, for instance).

In cases where the operator ID function is enabled, the assay reader device will now prompt the user to scan a barcode associated with an operator ID for each test event. For example, prior to prompting the user to input an assay test strip into the device for analysis, the assay reader device will display "SCAN OPERATOR ID" to the user, instructing the user to scan a barcode associated with the user's operator ID. The assay reader device can sequentially query the user to input particular types of information according to the previously-selected, customized configuration settings of the assay reader device. For example, after the user scans a barcode associated with an operator ID, the assay reader device can next prompt the user to scan a barcode associated with a specimen ID for the test event (see, for example, "SCAN SPECIMEN ID" display in FIG. 9), if the device was configured to request specimen ID information. In some cases, the assay reader device will not prompt the user to input an assay test strip for analysis until all information required by the particular configuration settings has been entered. In some cases, the assay reader device can display a summary of the configuration settings (see, for instance, the example display at the top of the middle column in FIG. 9).

A customizable reporting function can be handled at the server side or by one or more remote computing devices that are physically separate from the reader devices but receive information from the reader devices. For example, test result data and associated information from scanned barcodes can be stored in a database of one or more remote computing devices, for example a server system, and the remote computing device can produce customized reports with only fields of interest to the end user. An end user can include but is not limited to a user of the reader device, an administrator in a healthcare facility using the reader device, an entity managing remote server systems, and a public health organization.

Non-compliant test results (for example, having blank fields for any information required by the healthcare group internal standards or applicable regulations) can be flagged in the database. In some examples, statistical analysis can be performed on non-compliant results to identify common sources of non-compliance, such as but not limited to non-compliant test results issuing from a particular batch or lot of test strips, non-complaint information transmitted with test results by a particular healthcare provider or testing location, and non-compliance with reporting frequency or some other deficiency. Such information can be provided automatically in some embodiments to a healthcare organization administrator to assist in developing plans for increased adherence to compliance standards. Compliance with specified information type requirements can facilitate more meaningful statistical analysis of compliant test results by standardizing the information collected from a number of different operators, facilities, or healthcare groups, for example in order to identify and track infectious disease trends for developing disease management plans.

Referring to FIG. 1A, Barcode and connectivity module 110 also includes a barcode reader 112 as described above and additionally a connectivity device, represented graphically by connectivity marker 114. The connectivity device can be a wireless communication device, such as a cellular modem, for accessing a publicly provided, publicly maintained data network. The publicly provided network could be a public telephone network, a public cellular network, or another suitable kind of publicly available data network. Barcode and connectivity module 110 can further include mechanical features for lockingly engaging corresponding features within the bay 132 of the base assay reader device 130 and electronic features for establishing electronic data communications with components of the base assay reader device 130. This can reduce administrative burden and overhead, as well as help reduce or minimize errors associated with manual results documentation and recording.

Though not illustrated, barcode and connectivity module 110 can include an information element as described above. The information element can function to identify the barcode scanning and network connectivity capabilities of barcode and connectivity module 110 to the assay reader device and/or to authenticate the barcode and connectivity module 110 as a module from a specific source or manufacturer.

The barcode and connectivity module 110 can provide all of the functionality and benefits of the barcode module 120 and additionally provide cellular or other wireless connectivity. Such connectivity can be used to document test results across multiple sites and integrate with an electronic medical record (EMR) HIS, LIS, and/or other health record database. For example, in some embodiments test results can be sent to a centralized, server-based database and then routed to the appropriate medical record, hospital, or laboratory database. The automatic transmission of test results can ensure automated documentation of the results to patient records. In addition, automatic transmission of test results can provide real-time alerts to designated medical personnel, for example a doctor of the patient, of potentially dangerous health conditions of the patient, enabling rapid diagnosis and treatment. Further, automatic transmission of test results to public health organizations can enable real-time aggregation and analytics of test result data to identify and possibly curb infectious disease trends. Such medical information transmission can be accomplished via a secure end-to-end connection complying with HIPAA, HITECH, ISO 27001:2013 cybersecurity guidelines, or other industry standards, and data may be encrypted prior to transmission. Cellular or satellite connectivity can enable for rapid transmission of test results from locations even outside of standard clinical settings.

Cartridge 140 can secure an assay 144 for proper alignment within the base assay reader 130. As illustrated, cartridge 140 can include a window for exposing a test region of the assay 144. The assay 144 can be an immunoassay, for example implementing colloidal metal particle technology to furnish sensitivity and strong test performance. The assay 144 can alternatively be a bioassay, ligand binding assay, or any other type of diagnostic test that can be optically imaged to determine a test result. Cartridge 140 can also include a barcode 142 for providing test information, for example a type of test, that can be used in some embodiments to configure an automated process run by the device 130 for determining a result of the assay. The user can scan the barcode 142 of the cartridge 140 using the barcode scanner of a module lockingly engaged with the base assay reader 130, such as the barcode scanner of barcode module 120 or barcode and connectivity module 110, as a way to input information into the base assay reader device 130. Such information can include one or more of patient and/or physician identification information, information relating to the assay test, a barcode password for unlocking functions of the base assay reader device 130, and the like.

The base assay reader device 130 can include one or more additional data communications ports (not illustrated), for example a USB port. The port can be set up as a general purpose hardware interface for the base assay reader device 130. Using this interface, the base assay reader device 130 can support external peripherals, for example a printer or a keyboard. The port can enable the base assay reader device to be connected to a PC for data download. For example, when the base assay reader device is connected to a PC via a USB interface, the reader device can function like a USB drive. In addition, the end user can update the reader device firmware by connecting a USB drive containing the latest firmware revisions to the USB port. Furthermore, the USB port offers a convenient way to upload assay calibration data into the reader device, for example lot specific calibration data.

Though not illustrated, additional module options can be available, for example a connectivity module without barcode features, a wired connection module, and modules having power storage features for increasing device battery life, to name a few examples. In some embodiments the module can be or include a printer. In some embodiments, a module can be or include a separate detection unit. Such a detection unit module may be used to run the same or a different type of test than the base assay reader device 130. In some embodiments the module can be an incubator for incubating the assay before determining a test result. For example, for lateral flow assays, an incubator module may be used to hold the assay and track the development time before providing a reminder or indication to the user to remove the cartridge and insert it into the base assay reader device 130 for reading. For molecular assays, the incubator module may be used for sample preparation and incubation.

Example Data Network

Figure 2:
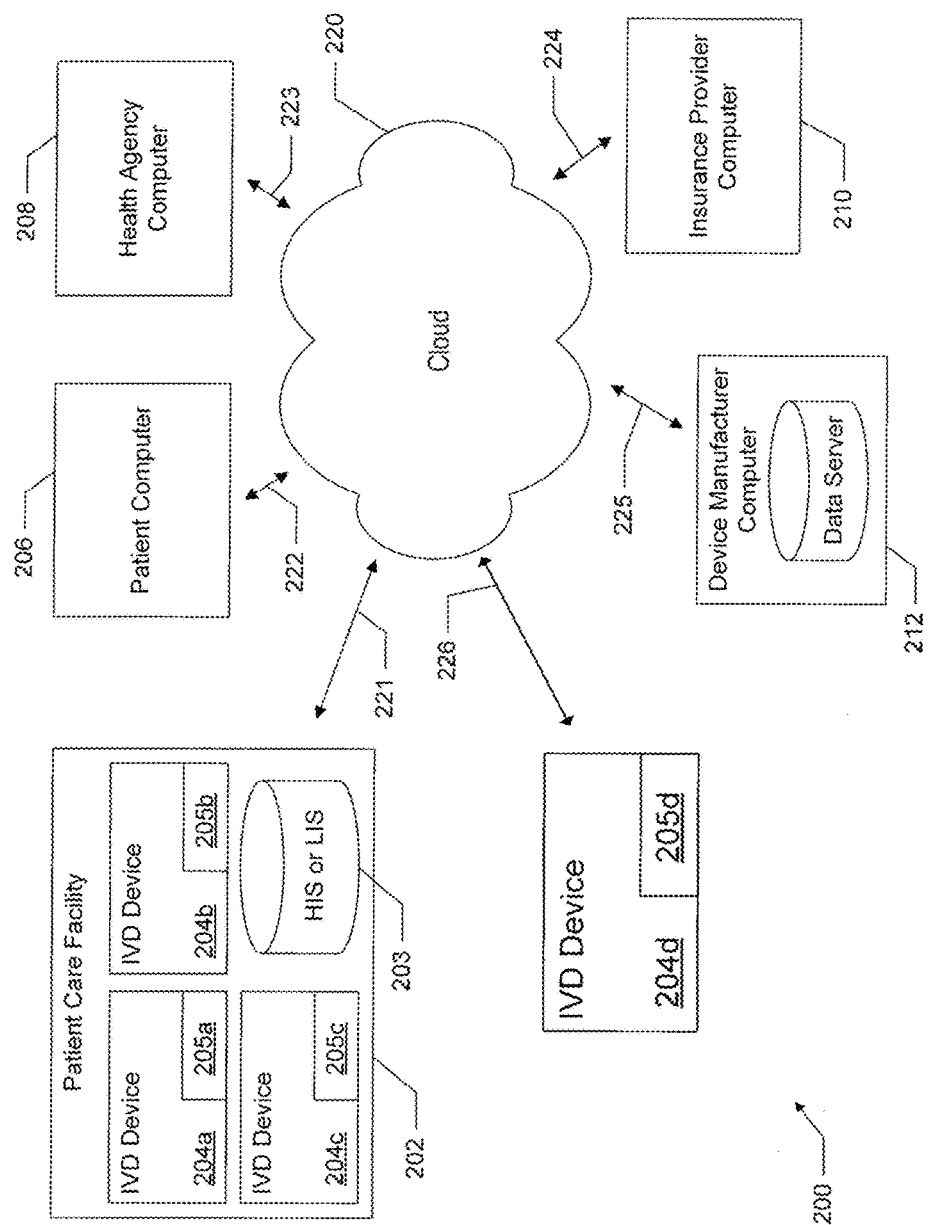
FIG. 2 illustrates a schematic block diagram of an example data network including the disclosed assay reader systems.

Referring now to FIG. 2, a schematic illustration of one networked embodiment of a system 200 is illustrated. In the illustrated embodiment, arrows between certain devices and a cloud 220, such as a Public Wide Area Network (WAN) or the Public Network, indicate that such devices are configured to engage in two-way communication via such a network. If a network element illustrated in FIG. 2 is associated with an arrow pointing to the network element and the cloud 220, that device is configured to both send data to another device via the cloud 220 and to receive data from another device via the cloud 220. For example, an arrow 226 indicates that an in vitro diagnostic (IVD) device 204*d* can be configured to engage in two-way communication with another device on the cloud 220. Although FIG. 2 illustrates certain devices to be configured to engage in two-way communication, this is illustrative only and is not intended to be limiting. For example, the in vitro diagnostic (IVD) device 204*d* can be configured to engage in one-way communication with another device via the cloud 220.

FIG. 2 illustrates an example schematic representation of a patient care facility 202. The patient care facility 202 can represent a patient facility, such as a hospital, doctor's office, or clinic, at which one or more diagnostic tests is applied or given to a patient. In the illustrated embodiment, the patient care facility 202 is shown as including or encompassing a Hospital Information System (HIS) or Laboratory information System (LIS) database 203. That is, in the illustrated embodiment, the patient care facility 202 maintains or otherwise provides access to an HIS or LIS database 203. In the illustrated embodiment, the HIS or LIS database 203 is a repository for test results, summary reports, or other data related to patients utilizing the patient care facility 202. In various embodiments, the HIS or LIS database 203 is additionally coupled with one or more processors (not shown) for performing certain processing tasks, such as analysis of data stored in the HIS or LIS database 203.

In the illustrated embodiment, the patient care facility 202 also includes a plurality of in vitro diagnostic (IVD) devices 204*a*, 204*b*, and 204*c*. However, as illustrated by IVD device 204*d*, the network environment 200 can also include IVD devices outside of the patient care facility setting. In one embodiment, the IVD devices are diagnostic test devices, such as devices configured for optically imaging lateral flow assay test strips having an applied biological sample and determining diagnostic test result information based on image data representing the test strips. It should be appreciated that any suitable IVD device could be advantageously used concurrently with the disclosed system.

As further illustrated in FIG. 2, each IVD device 204*a*, 204*b*, 204*c*, and 204*d* can include a network communication device 205*a*, 205*b*, 205*c*, or 205*d*, respectively. For example, the network communication devices 205*a*, 205*b*, 205*c*, and 205*d* can be provided through an insertable accessory module including a cellular modem or another transceiver device configured to communicate with the cloud 220. In one embodiment, an IVD device 204*a*, 204*b*, 204*c*, or 204*d* can establish an encrypted channel with another device on the cloud 220. For example, the IVD device 204*a* can establish an encrypted channel 084 with the cloud system 816 in FIG. 8. The IVD device 204*a*, 204*b*, 204*c*, or 204*d* can transmit a test result to the cloud system 816 on the cloud 220 via the encrypted channel. The cloud system 816 can store the test result in a HIS or LIS database 203. In another embodiment, the network communication devices 205*a*, 205*b*, 205*c*, and 205*d* enable the respective IVD devices to communicate with either one another, or with another network element, as disclosed herein. In addition, in one embodiment, the network communication devices 205*a*, 205*b*, 205*c*, and 205*d* enable the respective IVD devices to communicate data indicative of diagnostic test results to remote resources, such as the HIS or LIS database 203 for storage and/or further analysis. Though not illustrated, some IVD devices may be equipped with a barcode scanner module, such as barcode module 120. In one implementation, results stored by such devices can be sent to a patient computer 206. In another implementation, the network communication devices 205*a*-205*d* can be connected to the IDV devices 204*a*-204*d* via USB connections.

The system 200 of FIG. 2 indicates, by arrow 221, that the patient care facility 202 (and the IVD devices/HIS or LIS database contained therein) is configured to communicate via the cloud 220. In one embodiment, one or more of the Public Wide Area Network and the Public Network limits, at least in part, access to the network. Moreover, in one embodiment, the disclosed system 200 enables communication between the patient care facility by encrypted or other secure data transmission protocols, as described herein.

System 200 also includes a patient computer 206, health agency computer 208, insurance provider computer 210, and device manufacturer computer 212. Each of these network elements are able to communicate with one another, directly or indirectly through one or more other devices, and with the patient care facility 202 via the cloud 220, as indicated by arrows 222, 223, 224, and 225, respectively. In one implementation, a Public Wide Area Network can communicate with a Public Network of another type, such as the Internet. For example, the devices illustrated in FIG. 2 can be configured to communicate with one another either via a Public Wide Area Network, a Public Network, or some combination thereof.

In the illustrated embodiment, each of the computers enables a different party to communicate with the device manufacturer computer 212 and the IVD devices 204*a*, 204b, 204c and HIS or LIS database 203. For example, the patient computer 206 enables patients to communicate with the device manufacturer computer 212, the health agency computer 208 enables one or more health agencies to communicate with the patient care facility 202, the insurance provider computer 210 enables an insurance provider to communicate with the patient care facility 202, and the device manufacturer computer 212 enables the manufacturer of the IVD devices to communicate with the patient care facility 202. The device manufacturer computer 212 can enable the IVD devices 204a, 204b, 204c, and 204d to communicate with a data server 212a coupled to the device manufacturer computer 212 to, among other things, receive necessary data, such as calibration data, firmware, or other software and data upgrades, when the need arises. In another embodiment, the IVD devices 204a-204d securely communicate with a cloud system, such as the cloud system 816 illustrated in FIG. 8.

In various embodiments, the system 200 enables the transmission and exchange of data including test results and additional data sent along with the test results. For example, the data transmitted among the various network elements of the system 200 could include diagnostic data and information, network information, hardware information, and environmental information as described above. In one embodiment, some or all of the data transmitted among the various elements of the illustrated system 200 are encrypted to prevent unwanted access to the transmitted data. In addition to protecting the data from interception and unwanted consumption, this encryption may also validate or maintain the integrity of the transmitted data, such as by providing a checksum or other mechanism to ensure that all transmitted data was received.

In one embodiment, the patient computer 206, health agency computer 208, insurance provider computer 210, and device manufacturer computer 212 are standard desktop or laptop computers accessible by the appropriate party. In another embodiment, one or more of the patient computer 206, health agency computer 208, insurance provider computer 210, and device manufacturer computer 212 are mainframe or server computers configured to handle large quantities of data and/or to provide complex processing and analysis routines. In this embodiment, the appropriate entity which is responsible for the illustrated computer device (e.g., the insurance company responsible for the insurance provider computer) can access some or all of the data uploaded from the IVD devices and stored within the system, depending on the purpose of the user's access. In another embodiment, one or more of the patient computer 206, health agency computer 208, insurance provider computer 210, and device manufacturer computer 212 are portable computers, such as personal digital assistants (PDAs) or cellular telephones, which are configured to enable users to access data from a handheld, portable device. In one embodiment, not shown, one or more medical professionals such as health care personnel staffing the patient care facility 202 access data communicated by the IVD devices 204a, 204b, 204c, and 204d using an appropriate handheld device, such as a PDA, cellular telephone, or other handheld, portable device. In this embodiment, appropriate health care personnel can have access to, or be actively made aware of, patient data immediately upon the patient sample being analyzed by a diagnostic test using an IVD device. It should be appreciated that in various embodiments, entities other than those of the illustrated network elements in FIG. 2 may be able to access the data uploaded by the IVD devices as necessary to perform those entities' respective tasks.

In one embodiment, as discussed above, an IVD device is configured to upload data to one or more database servers. The database servers may be configured to archive test results, aggregate test results into summary reports, or analyze test results for spatial, temporal, or other correlations. These database servers may additionally be configured to perform other analyses on the data, as appropriate, depending upon the type of data uploaded and the goals of the parties managing and implementing the database servers. The ability of IVD devices to upload data directly to database servers via the disclosed connectivity modules results in a number of advantages of the disclosed system. First, patient care facilities can obtain test results from database servers through secure Internet or other network connections and store the retrieved results in their own databases (e.g., their own HIS or LIS databases). In addition, the aggregated test reports available due to the processing of the database servers are of value to public health agencies like the CDC, FDA, and WHO. Such reports can be provided in real-time due to the ability of the disclosed IVD devices to directly and automatically communicate diagnostic test result data to database servers.

Example Assay Reader Device

Figure 3:
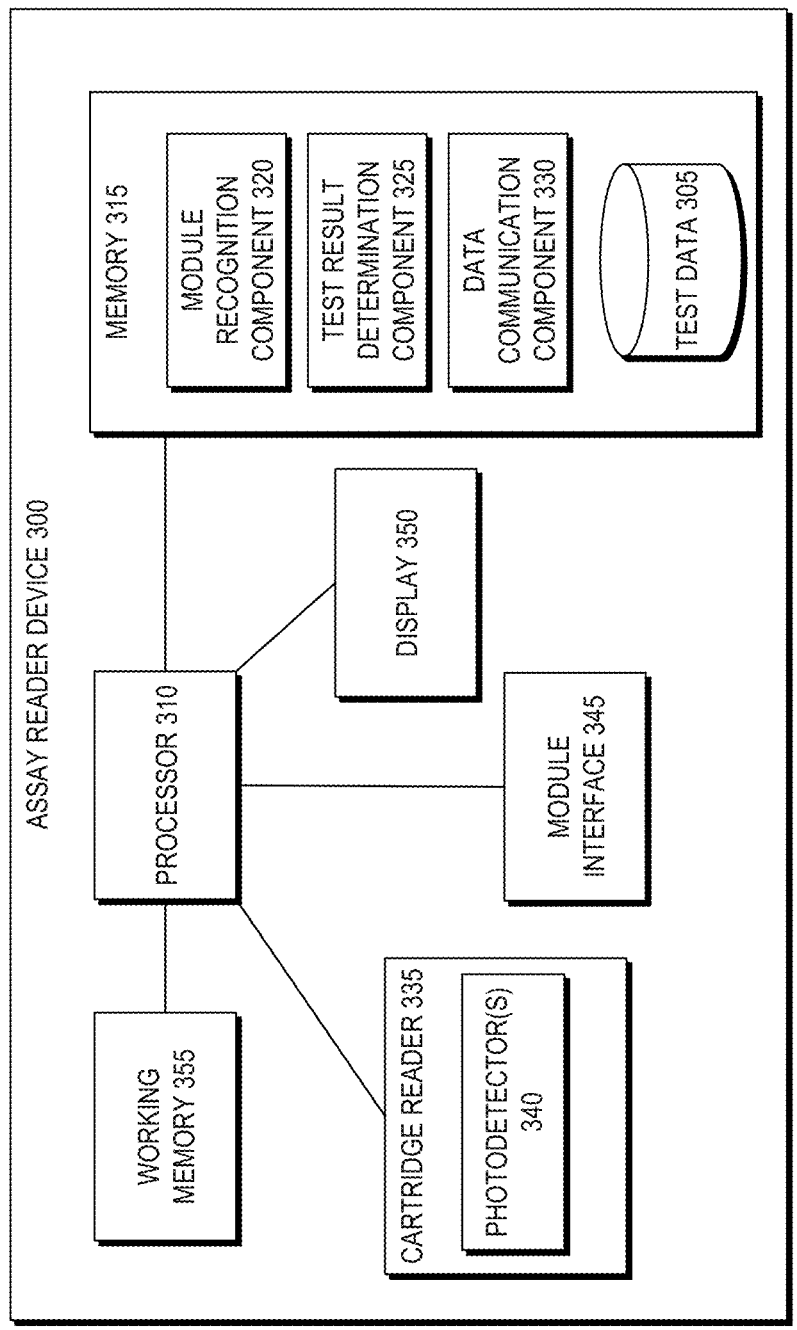
FIG. 3 illustrates a schematic block diagram of an example assay reader device.

FIG. 3 illustrates a schematic block diagram of one possible embodiment of internal components of an example assay reader device 300. The components can include a processor 310 linked to and in electronic communication with a memory 315, working memory 355, cartridge reader 335, module interface 345, and display 350.

Module interface 345 can include circuitry for reading information from an information element of an inserted module and transferring that information to processor 310 for analysis or validation. Thus, module interface 345 can provide a first signal path usable by device 300 for identifying characteristics of a connected module, the characteristics indicative of presence of a barcode scanner in the connected module and connectivity capabilities of the connected module. Module interface 345 can also include a path for establishing electronic communications with the barcode reader, network transceiver, power supply, or other electronic components of an inserted module. Thus, module interface 345 can provide a second signal path configured to receive barcode data from the connected module, the barcode data representing a barcode imaged by the connected module and/or information or instructions represented by the barcode.

The cartridge reader 335 can include one or more photodetectors 340 for reading an assay held in an inserted cartridge and optionally any information on the inserted cartridge, for example a barcode printed on the cartridge. The cartridge reader 335 can send image data from the one or more photodetectors to the processor 310 for analysis of the image data representing the imaged assay to determine a test result of the assay. The cartridge reader 335 can further send image data from the one or more photodetectors representing the imaged cartridge for use in determining which one of a number of automated operating processes to implement for imaging the assay and/or analyzing the image data of the assay. The photodetector(s) 340 can be any device suitable for generating electric signals representing incident light, for example a PIN diode or array of PIN diodes, a charge-coupled device (CCD), or a complementary metal oxide semiconductor (CMOS) sensor, to name a few examples. The cartridge reader 335 can also include a component for detecting cartridge insertion, for example a mechanical button, electromagnetic sensor, or other cartridge sensing device. An indication from this component can instruct the processor 310 to begin an automated assay reading process without any further input or instructions from the user of the device 300.

Processor 310 can be configured to perform various processing operations on image data received from the cartridge reader 335 and/or module interface 345 in order to determine and store test result data, as will be described in more detail below. Processor 310 may be a general purpose processing unit implementing assay analysis functions or a processor specially designed for assay imaging and analysis applications. The processor 310 can be a microcontroller, a microprocessor, or ASIC, to name a few examples, and may comprise a plurality of processors in some embodiments.

As shown, the processor 310 is connected to a memory 315 and a working memory 355. In the illustrated embodiment, the memory 315 stores module recognition component 320, test result determination component 325, data communication component 330, and test data repository 305. These modules include instructions that configure the processor 310 of device 300 to perform various module interfacing, image processing, and device management tasks. Working memory 355 may be used by processor 310 to store a working set of processor instructions contained in the modules of memory 315. Alternatively, working memory 355 may also be used by processor 310 to store dynamic data created during the operation of device 300.

As mentioned above, the processor 310 may be configured by several modules stored in the memory 315. The module recognition component 320 may include instructions that control the electronic communications between the processor and the module interface 345. For example, module recognition component 320 may include instructions that call subroutines to configure the processor 310 to read an information element of an inserted module to authenticate the module as compatible with the device 300 and determine capabilities of the inserted module. The test result determination component 325 can include instructions that call subroutines to configure the processor 310 to analyze assay image data received from the photodetector(s) 340 to determine a result of the assay. For example, the processor can compare image data to a number of templates or pre-identified patterns to determine the test result. In some implementations, test result determination component 325 can configure the processor 310 to implement adaptive read processes on image data from the photodetector(s) 340 to improve specificity of test results and to reduce false-positive results by compensating for background and non-specific binding.

The data communication component 330 can determine whether a module has been inserted into the device that enables wireless data transmission and can manage transmission of test result data to determined personnel and/or remote databases. For example, test result data transmission can be based on barcode data received together with the assay image, where the assay image is used to generate the test result and is stored in association with the test result, and wherein the barcode data is further stored in association with the test result. If the device 300 is not coupled with a network-communication-enabled module, the data communication component 330 can cause local storage of test results and associated information in the test data repository 305. If a local wired or wireless connection is established between the device 300 and another computing device, for example a hospital, clinician, or patient computer, the data communication component 330 can prompt a user of the device 300 to scan a password barcode using an inserted module in order to access the data in the repository 305.

The processor 310 can be configured to control the display 350 to display captured image data, imaged barcodes, test results, and user instructions, for example. The display 350 may include a panel display, for example, a LCD screen, LED screen, or other display technologies, and may implement touch sensitive technologies.

Processor 310 may write data to data repository 305, for example data representing captured images of barcodes and assays, instructions or information associated with imaged barcodes, and determined test results. While data repository 305 is represented graphically as a traditional disk device, those with skill in the art would understand that the data repository 305 may be configured as any storage media device. For example, data repository 305 may include a disk drive, such as a hard disk drive, optical disk drive or magneto-optical disk drive, or a solid state memory such as a FLASH memory, RAM, ROM, and/or EEPROM. The data repository 305 can also include multiple memory units, and any one of the memory units may be configured to be within the assay reader device 300, or may be external to the device 300. For example, the data repository 305 may include a ROM memory containing system program instructions stored within the assay reader device 300. The data repository 305 may also include memory cards or high speed memories configured to store captured images which may be removable from the device 300.

Although FIG. 3 depicts a device having separate components to include a processor, cartridge reader, module interface, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 3 illustrates a number of memory components, including memory 315 comprising several modules and a separate memory 355 comprising a working memory, one of skill in the art would recognize several embodiments utilizing different memory architectures. For example, a design may utilize ROM or static RAM memory for the storage of processor instructions implementing the modules contained in memory 315. The processor instructions may be loaded into RAM to facilitate execution by the processor 310. For example, working memory 355 may comprise RAM memory, with instructions loaded into working memory 355 before execution by the processor 310.

Example Operations Process of An Assay Reader Device

Figure 4:
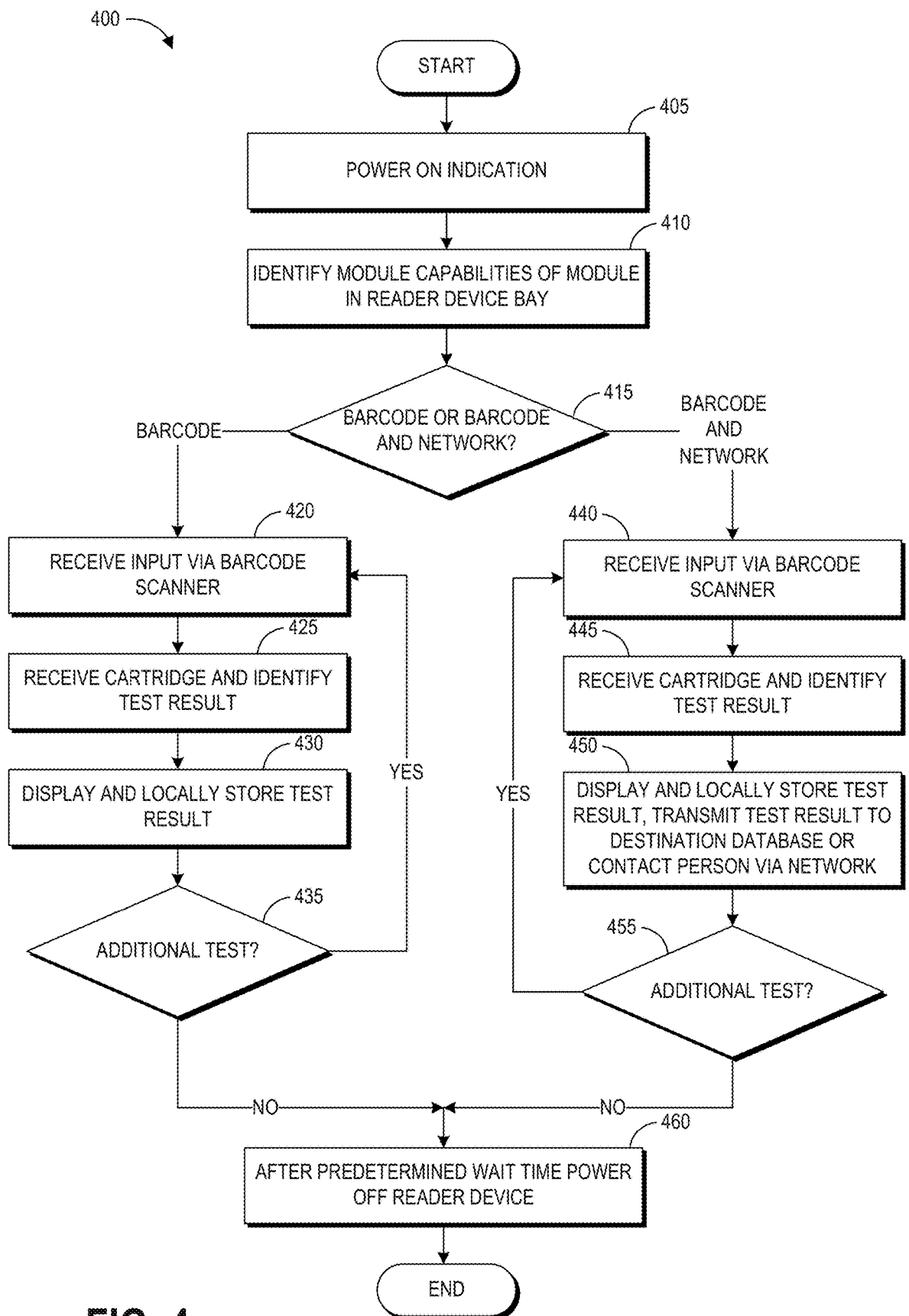
FIG. 4 is a flowchart depicting an example operations process of an assay reader device as disclosed herein.

FIG. 4 is a flowchart depicting an example operations process 400 of an assay reader device as disclosed herein. The process 400 can be implemented by an assay reader device 130 and/or processor 310 in some embodiments.

At block 405, the processor 310 can receive a power on indication, for example in response to a user pressing a single button located on an assay reader device.

At block 410, the processor can identify whether a module is inserted into a bay of the assay reader device and, if so, can identify the capabilities of the inserted module. As described above, these capabilities can include one or more of barcode scanning and network connectivity including cellular or satellite network connectivity.

At decision block 415, the processor 310 can identify whether the inserted module capabilities include barcode scanning or barcode scanning and network connectivity.

If the inserted module capabilities include barcode scanning, the process 400 can transition to block 420 to receive input via a barcode scanner of the inserted module. Such input can include information for storage in association with test results and/or information that configures the operations of the assay reader device, for example instructions regarding imaging procedures for acquiring image data of an inserted assay. In some embodiments device operation can be configured via a pattern of button presses as described above. At block 425, the process 400 can include receiving an assay test holding cartridge in a receiving aperture within the assay reader device, imaging the assay, and determining a test result based on the image data representing the assay. Block 425 can be implemented as any of the disclosed reader operation modes, such as but not limited to an end-point read mode or a walkaway mode. At block 430 the processor 310 can display and locally store the test result and any associated data.

At decision block 435 the processor can determine whether an additional test is to be performed, for example by receiving an indication that an additional barcode has been scanned (by looping back to block 420) or that an additional cartridge has been inserted (by looping back to block 425). In such instances the process can loop back through blocks 420-430, in the order shown or with blocks 420 and 425 switched.

If the inserted module capabilities include barcode scanning and network connectivity, the process 400 can transition to block 440 to receive input via a barcode scanner of the inserted module. Such input can include information for storage in association with test results and/or information that configures the operations of the assay reader device, for example instructions regarding imaging procedures for acquiring image data of an inserted assay or instructions regarding where test result data should be transmitted. In some embodiments device operation can be configured via a pattern of button presses as described above. At block 445, the process 400 can include receiving an assay test holding cartridge in a receiving aperture within the assay reader device, imaging the assay, and determining a test result based on the image data representing the assay. Block 445 can be implemented as any of the disclosed reader operation modes, for example an end-point read mode or a walkaway mode.

At block 450 the processor 310 can display and locally store the test result together with any associated data, for example an image of the assay used to generate the test result and additional information provided via a scanned barcode. Additionally or alternatively, the processor 310 can display and transmit the test result and optionally any associated data to a destination database or contact person via a network. For example, this can be accomplished through the connectivity module 110 inserted to and in electronic communication with base assay reader device 130 in some embodiments.

At decision block 455 the processor can determine whether an additional test is to be performed, for example by receiving an indication that an additional barcode has been scanned (by looping back to block 440) or that an additional cartridge has been inserted (by looping back to block 445). In such instances the process can loop back through blocks 440-450, in the order shown or with blocks 440 and 445 switched.

If, at either of blocks 435 or 455, the processor 310 determines that no additional test is to be performed (for example by inactivity of any of the sensors of the assay reader device), then the process 300 can transition to block 460. At block 460 the processor 310 can wait for a predetermined time period before powering off the assay reader device.

Example Hospital Workflow

Figure 5A:
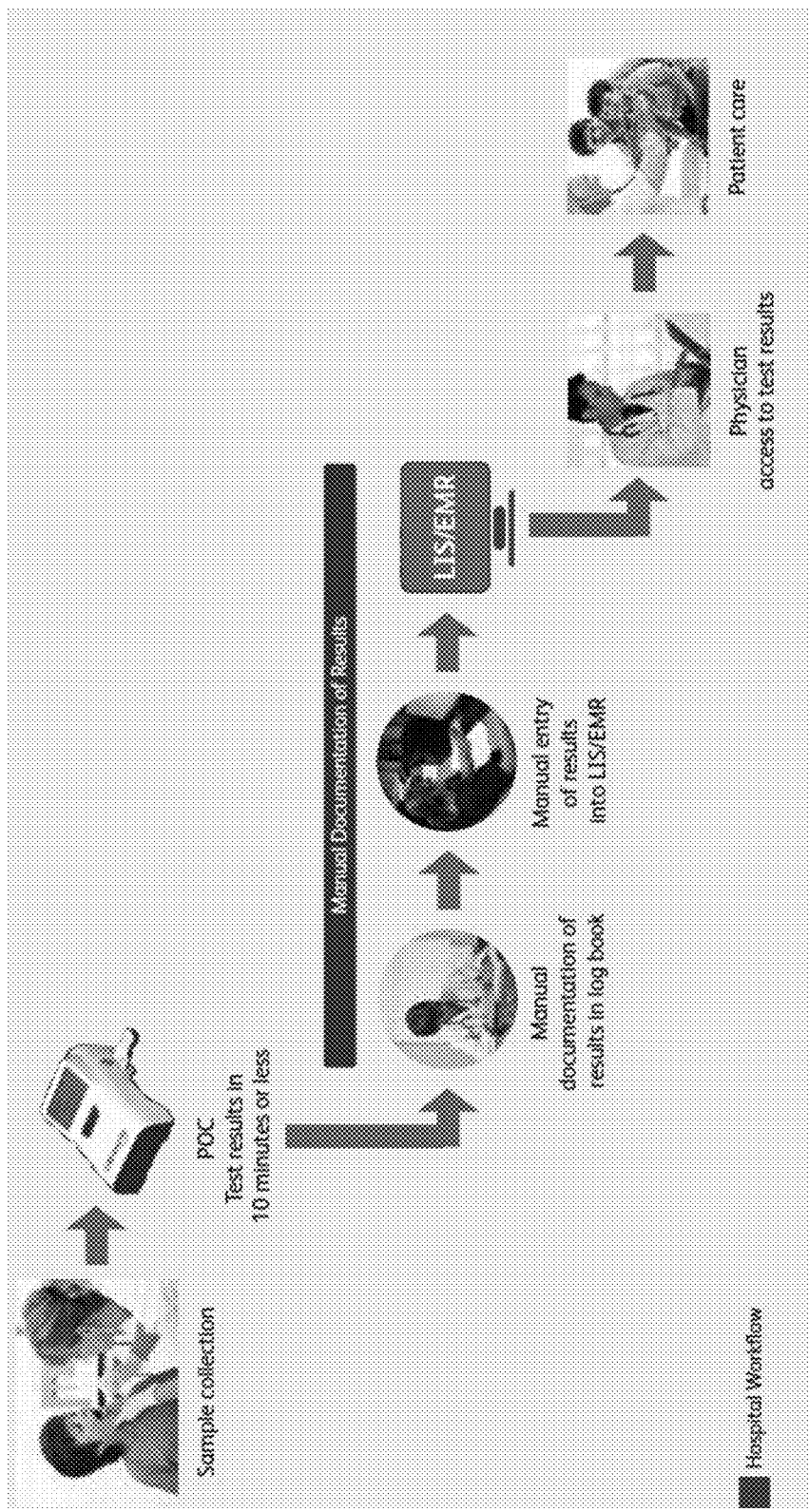
FIG. 5A illustrates an example hospital workflow without a wireless point of care testing solution.

FIG. 5A illustrates an example hospital workflow without a wireless point of care testing solution. As illustrated, a sample is collected and test results are provided at the point of care. Embodiments of a reader device described herein can provide test results in ten minutes or less. Subsequently, in order to provide manual documentation of results, the results are manually documented in a log book and then manually entered into a laboratory information system or electronic medical record. After the results are entered into the laboratory information system or electronic medical record, the physician is able to access the test results and provide patient care. In such a workflow the physician must wait for the manual documentation to be complete before reviewing test results and providing care to the patient.

Figure 5B:
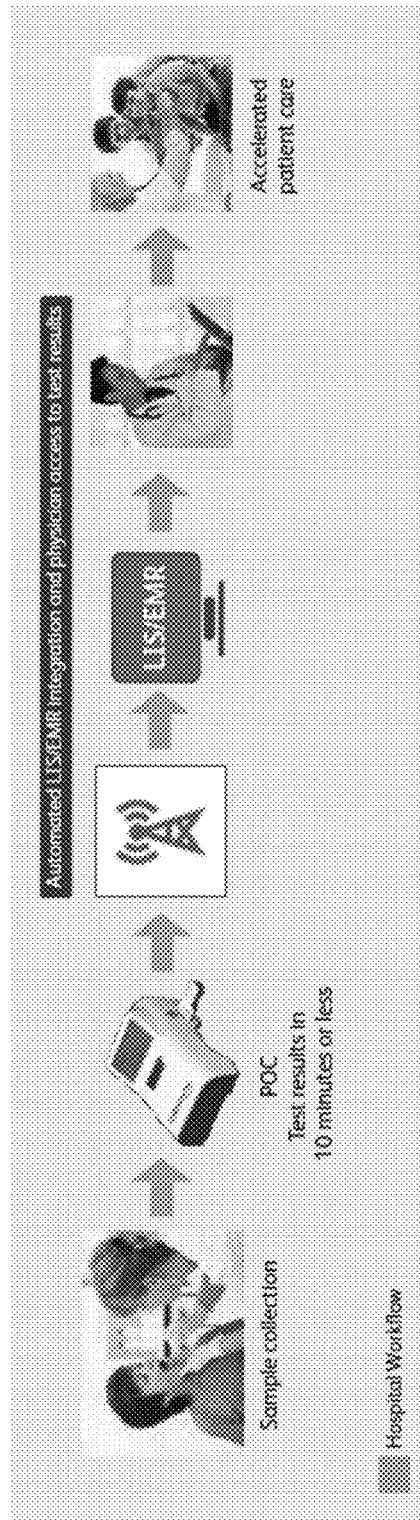
FIG. 5B illustrates an example hospital workflow implementing a streamlined workflow via the disclosed assay reader devices that provide a wireless point of care testing solution.

FIG. 5B illustrates an example hospital workflow implementing a streamlined workflow via the disclosed assay reader devices that provide a wireless point of care testing solution. As illustrated, a sample is collected and test results are provided at the point of care. Embodiments of a reader device including a network-communication-enabled module described herein can provide test results in ten minutes or less. From the point of care, the results are automatically transmitted via a network directly to a laboratory information system or electronic medical record. The transmitted results are immediately available to the physician at the point of care via the laboratory information system or electronic medical record, facilitating accelerated patient care. In this workflow, the physician is able to access the patient's test results while the patient is still in the office rather than having to wait for manual documentation of the test results, thereby enabling more rapid treatment of the patient.

One advantage of the base assay reader devices described herein is that each device can be upgraded at any time, for example by provision of a new module, providing a scalable platform to meet the growing needs of a healthcare group. A base assay reader device can incorporate other testing platforms and instruments via the module receiving bay. Further, a single assay reader device can be used for multiple functions via interchangeable modules. In one example, a health services provider can purchase and use the base assay reader device without any of the described modules. As the provider expands its capabilities, requires increased functionality, or additional purchasing resources become available, the provider can buy one or more modules as needed to meet its particular needs. The modules can be inserted into the base assay reader devices to quickly and easily expand the functionality of the devices, without any modification to the previously-acquired base assay reader device. As another example, a health services provider can purchase a kit having a base assay reader device and one or more modules, and later a new barcode scanner module may be developed with additional functionality. The provider can purchase the new barcode scanner whenever it wants and still use the previously-acquired base assay reader device with the old module changed out for the new module. In another example, the barcode scanner or some other component in a module may malfunction or break. A spare can be used with the base assay reader device while the first barcode scanner is repaired.

Other advantages of the disclosed base assay reader devices with network connectivity modules is that the single access-point integration with electronic medical records and laboratory information systems provides test results quickly, enabling decision making while the patient is on site. This automated documentation can facilitate accelerated patient care by accelerating physician access to test results, providing the physician with results almost immediately after the test is completed, regardless of testing location. The disclosed base assay reader devices with a barcode scanning module reduce transcription errors compared to systems that require manual entry of identifying information.

Example Workflow and Environment

Figure 6:
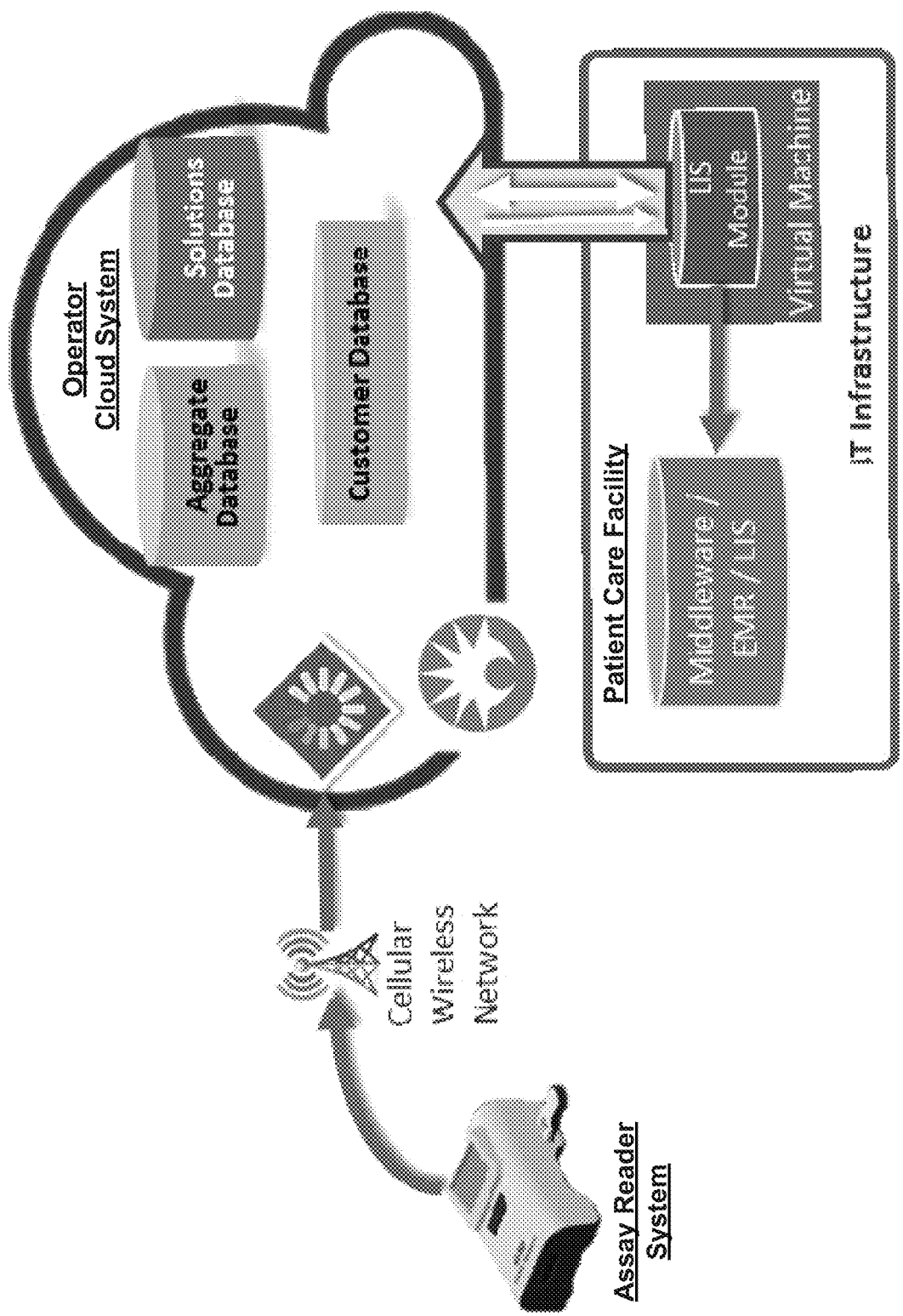
FIG. 6 illustrates an example data flow of the disclosed assay reader systems in an example environment.

One embodiment is a diagnostic assay device that communicates to a cloud-based server system. The cloud-based server includes a Cloud Connectivity Solution that enables an assay reader system or an in-vitro diagnostic device (for example, the BD Veritor™ Plus analyzer) to automatically document test results in a patient health record stored in a hospital or laboratory LIS or EMR. The connectivity solution has an in-lab and a cloud component. Test results received from connected assay reader system are validated, processed and delivered to the patient care facility's EMR, LIS or middleware. FIG. 6 illustrates an example data flow of the disclosed assay reader systems in an example environment.

In FIG. 6, an assay reader system is shown communicating through a cellular wireless network with an operator's cloud system. The cloud system includes a customer database for aggregating and storing test result data from a plurality of connected assay devices belonging to a specific customer, but located both in and outside of patient care facilities. The data in the customer database may be used for future analysis related to clinical or operational investigations for the devices belonging to that customer only. The cloud system may also include an aggregate database for aggregating and storing data from a plurality of connected assay devices across multiple customers. This can be used for future analysis, for example to determine geographic or other data relating to a particular infection pattern. Thus, if for example, a viral infection is spreading through the southwestern United States, the aggregate database may determine the location and spread of the infection from aggregated data from many assay devices showing infection rates and the known geographic locations of the assay devices. The cloud system also includes a solutions database that may be used to store information on customers and owners of the assay reader systems on the market. Also included in the cloud system may be an encryption system or module that secures the communication between the assay reader system and the operator cloud system.

FIG. 6 also shows a Patient Care Facility that is linked through a LIS module to the cloud system. This allows the Patient Care Facility to receive data and information relating to its patients from the cloud system. Thus, if one of the Patient Care Facility patients is tested using the assay reader system, that data is securely communicated to the cloud system, along with a patient identifier. The Patient Care Facility system may securely read, or send, the results of the assay run on the assay reader system so that it can store and manage the care of its patient. For example, the results of any test run on the assay reader system may be transmitted to the Patient Care Facility so that a health worker within the Facility would be notified and can take the proper steps to inform the patient and manage the patient's health care needs. As described in more details below, securing and encrypting the communications between the assay reader system and the cloud system, and also between the Patient Care Facility and the cloud system can lead to more robust communications and help the systems comply with HIPAA and other legal requirements for maintaining the confidentiality of patient information. Protocols for encrypting the communications between the assay reader system, the cloud system, and the Patient Care Facility can be based on the Hyper Text Transfer Protocol Secure (HTTPS) protocol and the Advanced Encryption Standard (AES) 256 bit encryption.

Figure 7:
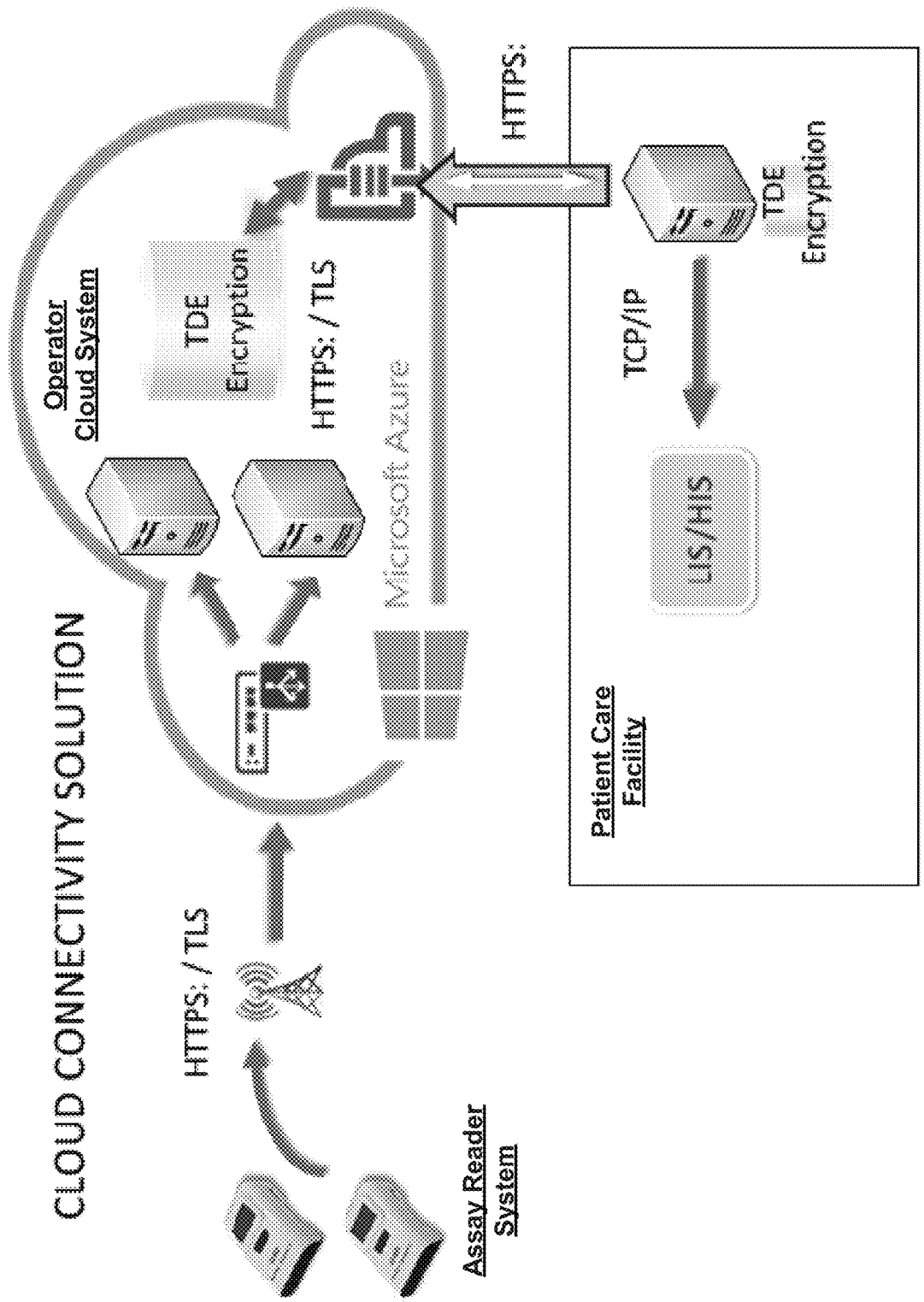
FIG. 7 illustrates an example data flow of the disclosed assay reader systems showing communication channels are encrypted.

FIG. 7 illustrates an example data flow of the disclosed assay reader systems showing communication channels are encrypted. As shown, a plurality of assay readers is connected through an encrypted Hyper Text Transfer Protocol Secure (HTTPS) or Transport Layer Security (TLS) channel to the operator cloud system. The data is sent to a series of servers that may store data within an encrypted data file inside of the cloud system. In addition, any data received can be stored in an encrypted format. For example, test results received can be encrypted using transparent data encryption (TDE), which is a technology designed to securely encrypt database files, prior to storage. TDE offers encryption at the file level so that data "at rest" is encrypted, and there is no requirement for the data to be transmitted between two components for it to be encrypted.

Virtual Machine

The in-lab application may be installed on a virtual server. The specifications of an example virtual machine are listed below.

Hardware Specifications

The illustrated Cloud Connectivity Solution cloud infrastructure uses redundant virtual machines in a high-availability set that optimizes performance and uptime. An operator of the Cloud Connectivity Solution is responsible for these machines including backup and monitoring of their performance.

The Cloud Connectivity Solution may include one virtual or physical machine installed on a patient care facility's infrastructure to process and deliver test results to the LIS, EMR, or middleware. The requirements for this machine may be:

Dual Core Processor;
8 GB RAM minimum (16 GB preferred);
Windows Server 2012 R2;
.NET 4.5.1;
IIS v8.5;
ASP .NET (installed as part of IIS);
Microsoft SQL 2012 Enterprise or MS SQL 2014 Enterprise (can use patient care facility's instance) with Mixed Mode Authentication enabled;
250 GB Disk Storage;
Internet Access; and/or
Google Chrome or IE 11.0.

In one implementation, the Patient Care Facility is responsible for controlling access to this machine. In some embodiments, it is recommended that access to this machine is limited to only necessary users and remote access is disabled. If service is necessary, authenticated remote access can be enabled for the service call, and then immediately removed after service is complete. Default passwords should be changed and the use of removable media restricted.

Operating Systems

Windows Server 2012 R2 may be used for all cloud and on premise machines.

Network Ports and Services—Cloud Machines

Cloud virtual machines can use standard internet ports 80 and 443. Additionally port 4155 is used for remote updates. Port 3389 (Remote Desktop Protocol (RDP)) and 8172 (Web Deploy) are opened only when needed.

The following services are deployed on cloud virtual machines:

Splunk forwarder, for app level monitoring;

Operations Management Suite (OMS) agent, for transmitting server data to OMS (and System Center Operations Manager (SCOM));

Snort agent, for intrusion detection;

Shavlik, for remote updates; and/or

Windows Antimalware for virus and malware protection.

Network Ports and Services—On-Premise Machines

Site (on premise) virtual or physical machines only require standard internet port 443 to be open. It may be recommended that the patient care facility does not open any other ports on this machine.

The following additional services that are required for on premise virtual or physical machines beyond those loaded as part of Windows Server 2012 R2: IIS v8.5.

Sensitive Data Transmitted

In one embodiment, the Cloud Connectivity Solution supports the following standards as it relates to data privacy and security of sensitive data:

The Defense Information Systems Agency Security Technical Implementation Guides;

NSA Guidelines for Information Assurance;

The FDA Guidelines for Cyber Security;

The Health Insurance Portability and Accountability Act (1996); and/or

The Health Information Technology for Economic and Clinical Health Act.

The following sensitive data elements may be transmitted from the assay reader system to the BD Cloud and from the BD Cloud to the Site machine:

Specimen ID—Configured to capture Accession Number or Patient's Medical Record Number (MRN); and/or Operator ID.

In some embodiments, the Cloud Connectivity Service treats all data as sensitive. All data can be encrypted during transmission using TLS over HTTPS. Data sent from the device uses TLS 1.1. All other network traffic uses TLS 1.2.

Sensitive Data Stored

In one example, the Cloud Connectivity Solution supports the following standards as it relates to data privacy and security of sensitive data:

The Defense Information Systems Agency Security Technical Implementation Guides;

NSA Guidelines for Information Assurance;

The FDA Guidelines for Cyber Security;

The Health Insurance Portability and Accountability Act (1996); and/or

The Health Information Technology for Economic and Clinical Health Act.

The following sensitive data elements are stored by the Cloud Connectivity Solution from results sent by the assay reader system:

Specimen ID—Configured to capture Accession Number or Patient's MRN; and/or

Operator ID

In some embodiments, the Cloud Connectivity Solution treats all data as sensitive. All data is encrypted at rest using MS SQL TDE with 256 bit encryption. This includes temporary stores such as queues.

Malware Protection

As an example, the Cloud Connectivity Solution can support the following standards as it relates to malware protection:

The Defense Information Systems Agency Security Technical Implementation Guides;

NSA Guidelines for Information Assurance;

The FDA Guidelines for Cyber Security; and/or

The Health Information Technology for Economic and Clinical Health Act.

Malware Protection—Cloud Machines

The Cloud Connectivity Solution may use Windows Defender for Anti-malware protection on all cloud virtual machines. Cloud virtual machines receive monthly updates of virus and malware definitions. Cloud machines may also use AppLocker to control access to the installation and running of applications.

Malware Protection—On-Premise Machines

Anti-Malware for on premise assets may be the responsibility of the patient care facility, including regular updates. It may be recommended that AppLocker or other mechanism be used to control access to the running of applications.

Authentication Authorization

The Cloud Connectivity Solution can support the following standards as it relates to authentication and authorization in one embodiment:

The Defense Information Systems Agency Security Technical Implementation Guides;

National Institute of Standards and Technology (NIST) "Framework for Improving Critical Security Infrastructure Cybersecurity" Feb. 12, 2014;

NSA Guidelines for Information Assurance;

The FDA Guidelines for Cyber Security;

The Health Insurance Portability and Accountability Act (1996); and/or

The Health Information Technology for Economic and Clinical Health Act.

In some implementations, the operator of the Cloud Connectivity Solution implements best practices for credential management and authentication. Access requires 2-factor identification using Active Directory Federated Services (ADFS). The operator enforces strong password policies including minimums, hashes, forced resets, lockouts and timeouts. Access is revoked for terminated employees or employees that change roles. Application components are secured through whitelisting and access tokens. All communications can be secured using TLS encryption.

The operator of the Cloud Connectivity Solution uses role-based access control (RBAC) for authorization. Each role has a specific limited functional scope and each user is assigned a single role.

Network Controls

The Cloud Connectivity Solution supports the following standards as it relates to network controls:

The Defense Information Systems Agency Security Technical Implementation Guides; and/or NSA Guidelines for Information Assurance.

The cloud servers that comprise the system adhere to The Defense Information Systems Agency Security Technical Implementation Guides (DISA STIGs) and are maintained accordingly for all versions of the Windows operation systems supported.

The operator of the Cloud Connectivity Solution may use Virtual Networks and IP restrictions to prevent access to application services that process sensitive data or communicate with repositories. All network traffic uses TLS 1.2 over HTTPS. Servers are protected by firewall systems, and scans are performed regularly to ensure that vulnerabilities are quickly found and patched. The operator may perform annual penetration testing to ensure security is maintained as vulnerabilities are discovered by the industry. All services have quick failover points and redundancy to ensure your data is safe.

On-premise machines may not require public facing internet endpoints. Applications running at client locations do not require inbound ports to traverse data between remote applications, services and devices and cloud application services. Outbound communications over TLS (port 443) are used for hybrid cloud and on premise communications. Adhering by the patient care facility may be recommended to adhere to The Defense Information Systems Agency Security Technical Implementation Guides (DISA STIGs) for institution supplied virtual or physical machines.

Encryption

The Cloud Connectivity Solution can support the following standards as it relates to encryption:

The Defense Information Systems Agency Security Technical Implementation Guides;
National Institute of Standards and Technology (NIST) "Framework for Improving Critical Security Infrastructure Cybersecurity" Feb. 12, 2014;
NSA Guidelines for Information Assurance;
The FDA Guidelines for Cyber Security;
The Health Insurance Portability and Accountability Act (1996); and/or
The Health Information Technology for Economic and Clinical Health Act.

All stored data may be encrypted using MS SQL TDE with 256 bit encryption. This includes temporary stores such as queues.

All test results sent from the assay reader system are encrypted using TLS 1.1 with AES 128 bit encryption.

All other data network traffic is encrypted using TLS 1.2 with AES 256 bit encryption.

Figure 8:
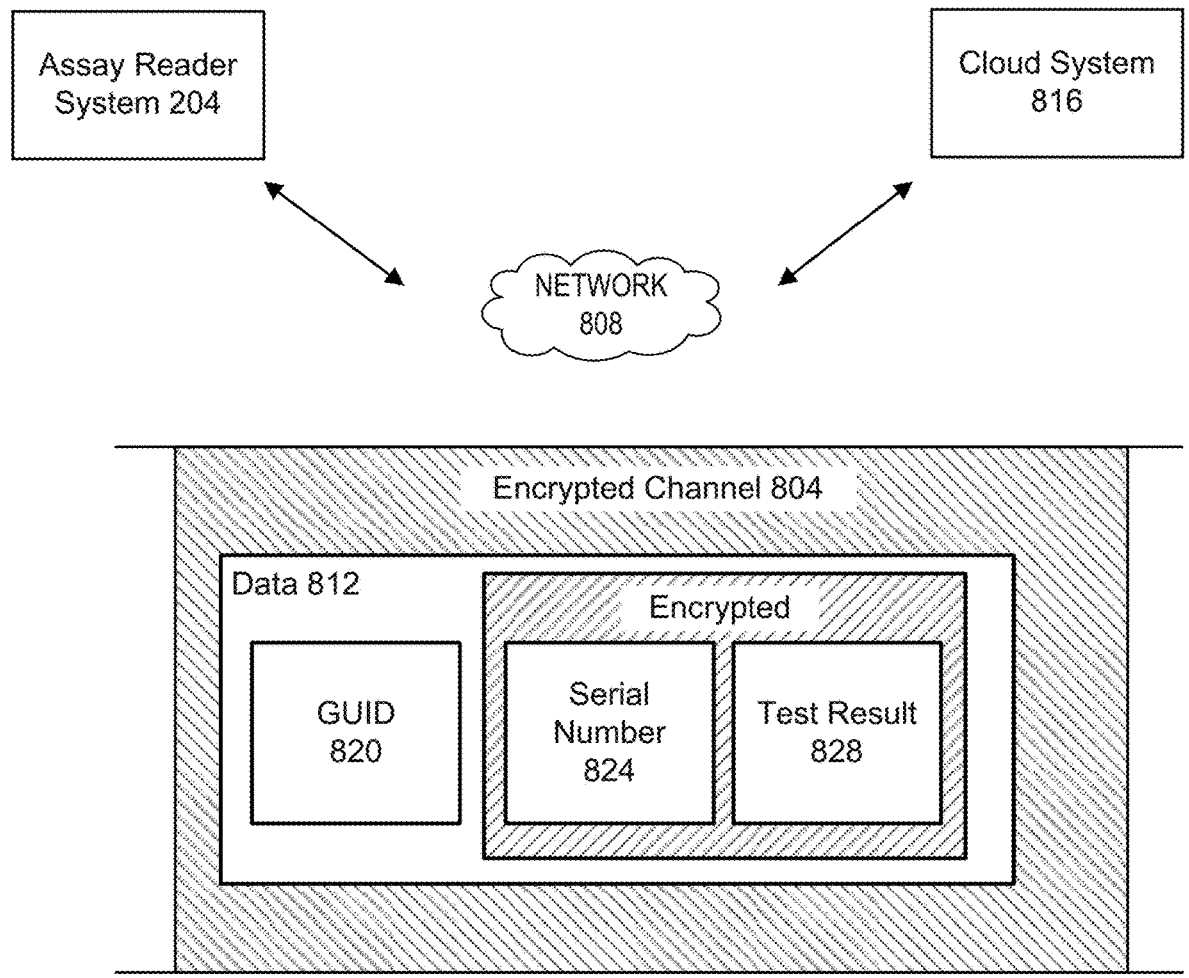
FIG. 8 shows a schematic illustration of an encrypted channel transmitting both encrypted and non-encrypted data through a communication network 808.

FIG. 8 shows a schematic illustration of an encrypted channel 804 transmitting both encrypted and non-encrypted data through a communication network 808. The cloud 220 in FIG. 2 is an example of the communication network 808. The network can include a public network (e.g., a cellular network) and/or a public wide area network. The encrypted channel 804 may utilize encryption methods to securely transmit data 812 from an assay reader system 204 to a cloud system 816. The cloud system 816 can implement the Cloud Connectivity Solution illustrated in FIGS. 6-7. The encryption methods utilized by the assay reader system 204 to create the encrypted channel 804 include symmetric key or asymmetric key public key cryptographic methods. For example, Transport Layer Security (TLS) 1.1 or 1.2 with Advanced Encryption Standard (AES) 256 bit encryption may be used create the encrypted channel 804. As another example, TLS 1.1 with AES 128 bit encryption may be used to encrypt test results from the assay reader system 204, and other data between the assay reader system 204 and the cloud system 816 may be encrypted using TLS 1.2 with AES 256 bit encryption. The encrypted channel 804 may be created using an encryption key that is unique for the assay reader system 204 such that no other assay reader system 204 utilizes the key to create an encrypted channel with the cloud system 816. In some embodiments, more than one assay reader systems share one encryption key for creating encrypted channels.

The data 812 transmitted through the encrypted channel 804 can include a number of data blocks. The data blocks can include a globally unique ID (GUID) or a universally unique ID (UUID) 820, a serial number 824 of the assay reader system 204, and test result 828. Additionally or alternatively, data 812 transmitted may include a manufacturer code, a model number of the assay reader system 204, a catalog number of a test, patient information including patient name, or technician information including the name of the technician who has performed the test. The GUID 820 may be unique to the assay reader system 204 such that no two assay reader systems have the same GUID 820. The GUID may be universally unique. The GUID 820 may not be visible on the assay reader system 204.

The serial number 824 may be unique to the assay reader system 204 such that no two assay reader systems can have the same serial number. The serial number 824 may be visible on the assay reader system 204. In some embodiments, the serial number may be advantageously encrypted (for example, because the serial number 824 may be visible on the assay reader system 204). The encryption key for encrypting the serial number 824 may be unique for the assay reader system 204 such other no other assay reader system utilizes that key for encrypting its serial number. In some embodiments, other data blocks (e.g., manufacturer code, model number, or catalog number of a test) may be encrypted.

The cloud system 816 may associate the GUID 820, the serial number 824, and the encryption key for encrypting the serial number 824 with the assay reader system 204. The cloud system 816 may store the association in a database configured to store authentication information. Accordingly, the assay reader system 204 can be authenticated. For example, the cloud system 816 can use the GUID 820 to determine the unique encryption key for that analyzer and use it to decrypt the encrypted serial number and encrypted test results received to obtain the serial number 824 and test results 828. Because the GUID 820 is uniquely associated with the encryption key for encrypting the serial number 824 and the test result 828, the cloud system 816 can decrypt the encrypted serial number and test result to obtain the serial number 824 and test results 828. To successfully authenticate that reader system 204 before processing any of the received test result 828, the GUID 820, the serial number 824, and the encryption key for encrypting the serial number must all match those of the assay reader system 204 stored in the database. As another example, each device 204 has two unique identifiers. One unique identifier is the device's serial number 824 that is on the outside of the device and is visible to the user. The other identifier is a GUID 820 that is embedded in the device 204 and only accessible programmatically. The two numbers are paired during manufacturing and only seen by authorized personnel. In addition, there is a unique encryption key that is private and assigned and associated with the serial number 824 and the GUID 820 during manufacture. An encryption algorithm such as the AES 256 encryption algorithm can be used to encrypt the a test result prior to secure transmission to the cloud system 816. Thus, in some implementations, a secure cellular communication enable the assay reader system 204 and the cloud system 816 to automate results documentation in patient health record (LIS/EMR) via the Cloud Connectivity Solution implemented by the cloud system 816.

After successful authentication of the assay reader system 204, the cloud system 816 may store the test result 828 in a database configured to store test results. The test result may be subsequently accessed or retrieved by the assay reader system 204. The assay reader system 204 needs to provide the GUID 820 and the encrypted serial number to access or retrieve the test result 828. The assay reader system 204 can provide information identifying the test result 828 to the cloud system 816 to access or retrieve the test result 828. Such information identifying the test result 828 can include a manufacturer code identifying a manufacturer of the assay reader system 204, a model number of the assay reader system 204, a catalog number of a test performed to generate the test result 828, patient information, and technician information. The stored test result 828 may be associated with other identifying information such as the catalog number of the test performed, the patient name, and/or the name of the technician who performed the test.

Audit Logging

Referring to FIGS. 6 and 7, the Cloud Connectivity Solution supports the following standards as it relates to logging and traceability:

The Defense Information Systems Agency Security Technical Implementation Guides;
NSA Guidelines for Information Assurance;
The FDA Guidelines for Cyber Security; and/or
The Health Information Technology for Economic and Clinical Health Act.

The following describes the logging capabilities of the system:

All security events are logged such as user logins, logouts, access requests, user invites and permission or role changes. This includes both successes and failures.

All database create, read, update and delete (CRUD) operations are logged.

All non-security based system activity is logged.

A healthcare institution controlled Cyber Log can be enabled on the Lab machine whereby all logging is written to a separate institution specified database. The institution controls the location and access to this database, and BD users cannot view or modify this log.

Debug logging (disabled by default) can be turned on to log finer granularity in system processing and details about program execution (used to troubleshoot abnormal operations).

All logs can be encrypted using MS SQL transparent data encryption (TDE) with 256 AES encryption. Access Control Levels (ACLs) are used to limit logging code from applications to write-only user accounts. Read-only user accounts will be used for application code that reads or produces reports on logs. This is restricted by access controls to appropriate accounts.

All security, activity, and change logs are saved a minimum of 90 days. Debug logs will be saved for as long as necessary to troubleshoot an issue. The healthcare institution controlled Cyber Log is maintained by the institution.

The Cloud Connectivity Solution logs significant details including user, date and time, event, result (where applicable), process/computer or other location information.

Remote Connectivity

Remote installation and support may be the primary method for on premise machine setup, configuration and troubleshooting.

Remote installation requires access to a virtual or physical machine for installation of the on premise components. Remote access should follow healthcare institution's IT recommendations for remote access.

Implementation, Configuration and Post Go-Live Support activities are performed by authorized Service Associates of the operator of the Cloud Connectivity Solution. These activities are performed with the assistance of the operator's Remote Support Services (RSS) tool.

RSS enables the operator to provide remote customer service. All communications, including remote access, occur within an SSL encrypted session over port 443 (outbound rule only).

Service Handling

Service Associates are trained on data privacy and the handling of PHI. Service Associates are granted appropriate role based access to the cloud and/or on premise components. Primary support personnel will have access to sensitive and operational data but not PHI. Furthermore, PHI exposure is not anticipated nor required for the installation, maintenance and normal support activities. Service Associates are trained on policies of the operator regarding the handling of PHI, including procedures for inadvertent exposure. All such interactions between Service Associates and the Cloud Connectivity Solution components may be audited in addition to remote activities performed with RSS.

End-of-Life and End-of-Support

There may be no end-of-life/end-of-support plans for the Cloud Connectivity Solution.

Secure Coding Standards

The operator of the Cloud Connectivity Solution may employ design controls to ensure security is embedded in the core software architecture. The operator adheres to current or future industry best secure coding standards including the Open Web Application Security Project (OWASP) Secure Coding Standards and routinely runs Static Code Analysis and Vulnerability Scans to ensure code meets the standards. The operator uses CheckMarx and HP Fortify for Static Code Analysis. BD uses Tenable Nessus and OpenVAS for Vulnerability Scanning.

System Hardening Standards

All cloud virtual machines support The Defense Information Systems Agency Security Technical Implementation Guides (DISA STIGs) and the NSA configuration standards for Department of Defense Information Security (DOD IA) and IA-enabled devices/systems for Windows Server 2012 R2.

The patient care facility is responsible for the on premise virtual or physical machine security according to their IT policies. The operator may recommend following The Defense Information Systems Agency Security Technical Implementation Guides (DISA STIGs) and the NSA configuration standards for DOD IA and IA-enabled devices/systems for Windows Server 2012 R2.

Risk Summary

Cacheable HTTPS Response may not be disabled.

Unless directed otherwise, browsers may store a local cached copy of content received from web servers. Some browsers, including Internet Explorer, cache content accessed via HTTPS. If sensitive information in application responses is stored in the local cache, then this may be retrieved by other users who have access to the same computer at a future time.

Implementing Systems and Terminology

Implementations disclosed herein provide systems, methods and apparatus for a modular, reconfigurable assay reader. One skilled in the art will recognize that these embodiments may be implemented in hardware or a combination of hardware and software and/or firmware.

The assay reader device may include one or more image sensors, one or more image signal processors, and a memory including instructions or modules for carrying out the processes discussed above. The device may also have data, a processor loading instructions and/or data from memory, one or more communication interfaces, one or more input devices, one or more output devices such as a display device and a power source/interface. The device may additionally include a transmitter and a receiver. The transmitter and receiver may be jointly referred to as a transceiver. The transceiver may be coupled to one or more antennas for transmitting and/or receiving wireless signals.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A cloud system for storing a test result, comprising:
   a computer-readable memory storing executable instructions; and
   one or more hardware-based processors programmed by the executable instructions to perform a method comprising:
      receiving a global unique identifier and an encrypted data block from a diagnostic test device via a communication channel, wherein the encrypted data block comprises a received serial number and a test result;
      obtaining a stored serial number and an encryption key associated with the global unique identifier;
      authenticating the diagnostic test device by decrypting the encrypted data block using the encryption key to obtain the received serial number and the test result and determining if the received serial number and the stored serial number are identical; and
      if the received serial number and the stored serial number are the same, then storing the test result in a storage device.

2. The cloud system of claim 1, wherein the global unique identifier is received as an unencrypted data block.

3. The cloud system of claim 1, wherein the test result is stored with information selected from the group consisting of: a manufacturer code identifying a manufacturer of the diagnostic test device, a model number of the diagnostic test device, a catalog number of a test performed to generate the test result, patient information, and technician information in the storage device.

4. The cloud system of claim 1, wherein the communication channel comprises a wireless communication channel.

5. The cloud system of claim 1, wherein the communication channel comprises an encrypted communication channel.

6. The cloud system of claim 5, wherein the encrypted communication channel comprises a Hyper Text Transfer Protocol Secure (HTTPS) or Transport Layer Security (TLS) channel.

7. The cloud system of claim 1, wherein the one or more hardware-based processors are further programmed by the executable instructions to perform a method comprising:
   receiving a second global unique identifier and a second encrypted data block from a second device, wherein the second encrypted block comprises a second received serial number and a second test result identifying information;

obtaining a second stored serial number and a second encryption key associated with the second global unique identifier;

authenticating the second device by decrypting the second encrypted data block using the second encryption key to obtain the second received serial number and the second test result identifying information; and determining whether the second received serial number and the second stored serial number are identical;

if the second received serial number and the second stored serial number are identical, then retrieving the second test result from the storage device using the test result identifier; and encrypting and sending the second test result to the second device using the second encryption key.

8. The cloud system of claim 7, wherein the second test result identifying information is selected from the group consisting of: a manufacturer code identifying a manufacturer of the second device, a model number of the second device, a catalog number of a test performed to generate the second test result, patient information, and technician information in the storage device.

9. The cloud system of claim 7, wherein the second device comprises a diagnostic test device.

10. The cloud system of claim 1, the wherein the encrypted communication channel comprises a Hyper Text Transfer Protocol Secure (HTTPS) or Transport Layer Security (TLS) channel.

11. An electronic method of storing a test result, comprising:

receiving a global unique identifier and an encrypted data block from a diagnostic test device via a communication channel, wherein the encrypted data block comprises a received serial number and a test result;

obtaining a stored serial number and an encryption key associated with the global unique identifier from a computer memory;

authenticating the diagnostic test device by decrypting the encrypted data block using the encryption key to obtain the received serial number and the test result and determining if the received serial number and the stored serial number are identical; and if the received serial number and the stored serial number are the same, then storing the test result in a storage device.

12. The method of claim 11, wherein the global unique identifier is received as an unencrypted data block.

13. The method of claim 11, wherein the test result is stored with information selected from the group consisting of: a manufacturer code identifying a manufacturer of the diagnostic test device, a model number of the diagnostic test device, a catalog number of a test performed to generate the test result, patient information, and technician information in the storage device.

14. The method of claim 11, wherein the communication channel is a wireless communication channel.

15. The method of claim 11, wherein the communication channel comprises an encrypted communication channel.

16. The method of claim 15, wherein the encrypted communication channel comprises a Hyper Text Transfer Protocol Secure (HTTPS) or Transport Layer Security (TLS) channel.

17. The method of claim 11, further comprising:

receiving a second global unique identifier and a second encrypted data block from a second device, wherein the second encrypted block comprises a second received serial number and a second test result identifying information;

obtaining a second stored serial number and a second encryption key associated with the second global unique identifier;

authenticating the second device by decrypting the second encrypted data block using the second encryption key to obtain the second received serial number and the second test result identifying information; and determining whether the second received serial number and the second stored serial number are identical;

if the second received serial number and the second stored serial number are identical, then retrieving the second test result from the storage device using the test result identifier; and encrypting and sending the second test result to the second device using the second encryption key.

18. The method of claim 17, wherein the second test result identifying information is selected from the group consisting of: a manufacturer code identifying a manufacturer of the second device, a model number of the second device, a catalog number of a test performed to generate the second test result, patient information, and technician information in the storage device.

19. The method of claim 17, wherein the second device comprises a diagnostic test device.

20. The method of claim 11, wherein the encrypted communication channel comprises a Hyper Text Transfer Protocol Secure (HTTPS) or Transport Layer Security (TLS) channel.

* * * * *

UNITED STATES PATENT AND TRADEMARK OFFICE
CERTIFICATE OF CORRECTION

PATENT NO. : 11,968,299 B2
APPLICATION NO. : 18/059219
DATED : April 23, 2024
INVENTOR(S) : Strett Roger Nicolson et al.

It is certified that error appears in the above-identified patent and that said Letters Patent is hereby corrected as shown below:

In the Specification

Column 26, Line 46, Delete "the a" and insert -- the --.

In the Claims

Column 31, Line 7, Claim 7, delete "information;" and insert -- information --.

Column 31, Line 25, Claim 10, delete "the wherein" and insert -- wherein --.

Column 32, Line 26, Claim 17, delete "information;" and insert -- information --.

Signed and Sealed this
Ninth Day of July, 2024

*Katherine Kelly Vidal*
*Director of the United States Patent and Trademark Office*